(12) United States Patent
Miller et al.

(10) Patent No.: US 11,241,555 B2
(45) Date of Patent: *Feb. 8, 2022

(54) BREATHING TUBE ASSEMBLIES WITH ADJUSTABLE ELBOW

(71) Applicant: FISHER & PAYKEL HEALTHCARE LIMITED, Auckland (NZ)

(72) Inventors: Jeremy Livingston Miller, Auckland (NZ); Dominique Richard D'Andrea, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 201 days.

This patent is subject to a terminal disclaimer.

(21) Appl. No.: 16/579,682

(22) Filed: Sep. 23, 2019

(65) Prior Publication Data

US 2020/0016359 A1 Jan. 16, 2020

Related U.S. Application Data

(63) Continuation of application No. 14/420,241, filed as application No. PCT/NZ2013/000138 on Aug. 8, 2013, now Pat. No. 10,456,547.

(Continued)

(51) Int. Cl.
*A61M 16/08* (2006.01)
*A61M 39/10* (2006.01)
(Continued)

(52) U.S. Cl.
CPC ...... *A61M 16/0816* (2013.01); *A61M 16/022* (2017.08); *A61M 16/08* (2013.01);
(Continued)

(58) Field of Classification Search
CPC .. A61M 16/00; A61M 16/08; A61M 16/0816; A61M 16/0825; A61M 16/0875;
(Continued)

(56) References Cited

U.S. PATENT DOCUMENTS 3,897,923 A 8/1975 Paepke et al.
4,151,864 A 5/1979 Thurman
(Continued)

FOREIGN PATENT DOCUMENTS

CN 1175891 3/1998
CN 101516300 8/2009
(Continued)

OTHER PUBLICATIONS

Office Action, Chinese Patent Application No. CN201380041787. X, dated Oct. 9, 2017, 7 pages.
(Continued)

*Primary Examiner* — Colin W Stuart
(74) *Attorney, Agent, or Firm* — Knobbe, Martens, Olson & Bear LLP

(57) ABSTRACT

Breathing tube assemblies for use with a respiratory therapy device, such as a continuous positive airway pressure (CPAP) device, includes an elbow that permits adjustment of a position of the breathing tube assembly relative to the respiratory therapy device. In some arrangements, the breathing tube assembly includes a breathing tube and a swivel elbow. The breathing tube is rotationally fixed relative to the respiratory therapy device and the swivel elbow rotatable relative to the breathing tube. In other arrangements, the breathing tube assembly includes an elbow that can be coupled to the respiratory therapy device in one of several possible positions.

22 Claims, 17 Drawing Sheets

Related U.S. Application Data

(60) Provisional application No. 61/681,083, filed on Aug. 8, 2012.

(51) Int. Cl.

| | |
|---|---|
| *A61M 16/00* | (2006.01) |
| *A61M 39/12* | (2006.01) |
| *F16L 3/12* | (2006.01) |
| *F16L 27/02* | (2006.01) |
| *F16L 3/08* | (2006.01) |
| *A61M 16/16* | (2006.01) |
| *A61M 16/10* | (2006.01) |
| *A61M 16/06* | (2006.01) |

(52) U.S. Cl.
CPC ........ *A61M 16/0875* (2013.01); *A61M 39/10* (2013.01); *A61M 39/1055* (2013.01); *A61M 16/06* (2013.01); *A61M 16/0825* (2014.02); *A61M 16/0883* (2014.02); *A61M 16/109* (2014.02); *A61M 16/1095* (2014.02); *A61M 16/16* (2013.01); *A61M 16/161* (2014.02); *A61M 39/12* (2013.01); *A61M 2039/1022* (2013.01); *A61M 2039/1027* (2013.01); *A61M 2039/1033* (2013.01); *A61M 2205/3368* (2013.01); *A61M 2205/36* (2013.01); *A61M 2205/6045* (2013.01); *A61M 2209/08* (2013.01); *F16L 3/08* (2013.01); *F16L 3/12* (2013.01); *F16L 3/1226* (2013.01); *F16L 27/02* (2013.01)

(58) Field of Classification Search
CPC .. A61M 16/0883; A61M 39/00; A61M 39/08; A61M 39/10; A61M 39/1011; A61M 39/1055; A61M 39/12; A61M 2039/1016; A61M 2039/1022; A61M 2039/1027; A61M 2039/1033; F16L 3/1226; F16L 3/12; F16L 3/08; F16L 27/02; F16L 27/023; F16L 35/00
See application file for complete search history.

(56) References Cited

U.S. PATENT DOCUMENTS

| | | | |
|---|---|---|---|
| 4,686,354 A | 8/1987 | Makin | |
| 4,889,168 A * | 12/1989 | Kerzich | F16L 35/00 138/103 |
| 5,509,409 A | 4/1996 | Weatherholt | |
| 5,682,881 A | 11/1997 | Winthrop | |
| 5,755,578 A | 5/1998 | Contant et al. | |
| 6,953,354 B2 | 10/2005 | Edirisuriya et al. | |
| 9,131,815 B2 | 9/2015 | Genoa et al. | |
| 10,456,547 B2 | 10/2019 | Miller et al. | |
| 2004/0261797 A1 | 12/2004 | White | |
| 2007/0277825 A1 | 12/2007 | Bordewick et al. | |
| 2009/0133697 A1 | 5/2009 | Kwok et al. | |
| 2010/0000538 A1 | 1/2010 | Edwards et al. | |
| 2010/0065051 A1 | 3/2010 | Potharaju et al. | |
| 2011/0023874 A1 * | 2/2011 | Bath | A61M 16/0816 128/202.22 |
| 2011/0146685 A1 | 6/2011 | Allan | |
| 2015/0136127 A1 * | 5/2015 | Dimatteo | A61M 16/06 128/202.27 |

FOREIGN PATENT DOCUMENTS

| | | |
|---|---|---|
| CN | 101772362 | 7/2010 |
| DE | 895692 | 11/1953 |
| DE | 102006011151 | 9/2007 |
| EP | 1369141 | 12/2003 |
| JP | 61-232864 A | 10/1986 |
| JP | 2005-525145 | 8/2005 |
| JP | 2009-529378 | 8/2009 |
| JP | 2010042307 | 2/2010 |
| JP | 3161849 U | 7/2010 |
| WO | WO 2004095666 | 11/2004 |
| WO | WO 2012160477 | 11/2014 |

OTHER PUBLICATIONS

Office Action, Chinese Patent Application No. CN201380041787.X, dated Jun. 12, 2018, 12 pages.
Notification of Reexamination, Chinese Patent Application No. CN201380041787.X, dated Jan. 17, 2020, 14 pages.
Board Opinion, Chinese Patent Application No. CN201380041787.X, dated Jul. 24, 2020, 14 pages.
Board Decision, Chinese Patent Application No. CN201380041787.X, dated Dec. 14, 2020, 1 page.
European Search Report, PCT/NZ2013000138, dated Apr. 1, 2018 in 8 pages.
State Intellectual Property Office of the People's Republic of China, Search Report, Application No. 201380041787.X, dated Mar. 30, 2017 in 16 pages.
Intellectual Property Office of Great Britain, Application No. GB1500734.7, Examination Report, dated May 15, 2017, in 5 pages.
Japanese Examination Report and English Translation; JP 2015-526495; dated Jul. 31, 2017; 9 pages.
Philips Respironics 'System One Heated Humidifier—User Manual', 2011, pp. 1-16, [retrieved on Nov. 25, 2013] from the internet; URL: http://www.cpapxchange.com/cpap-machines-blap-machines/system-one-60-series-cpap-humidifier-manual.pdf front cover, pp. 3-4 and 6.
International Search Report; Application No. PCT/NZ2013/000138; filed Aug. 8, 2013.
Search Report, European Patent Application No. EP20198725.2, dated Dec. 14, 2020, 7 pages.
Examination Report issued in Canadian Application No. 2,879,391 dated Aug. 28, 2020.
Canadian Office Action issued in CA 2903966 dated Oct. 27, 2020.
Chinese Office Action issued in CN201810946387.8 dated Nov. 2, 2020.

* cited by examiner

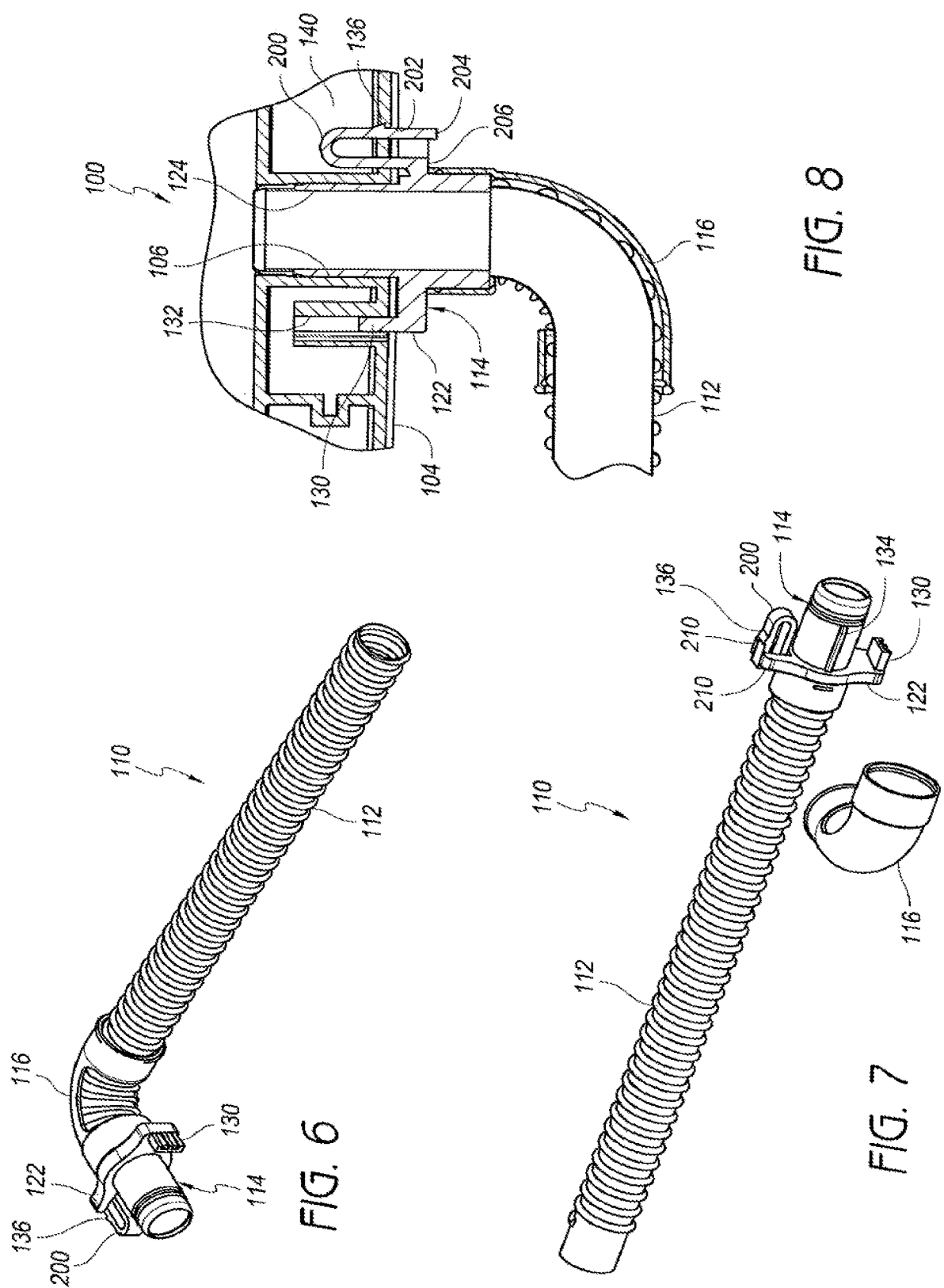

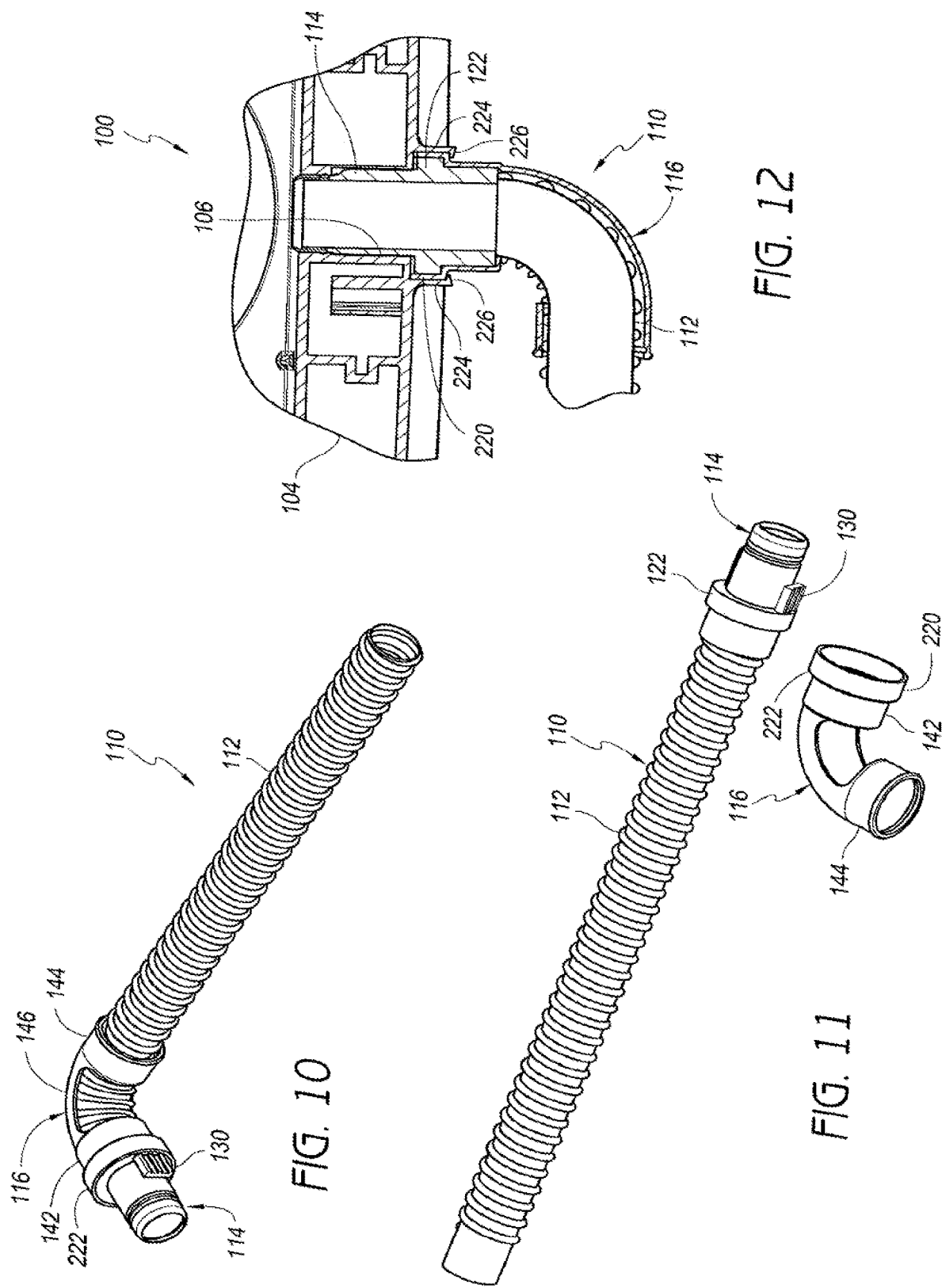

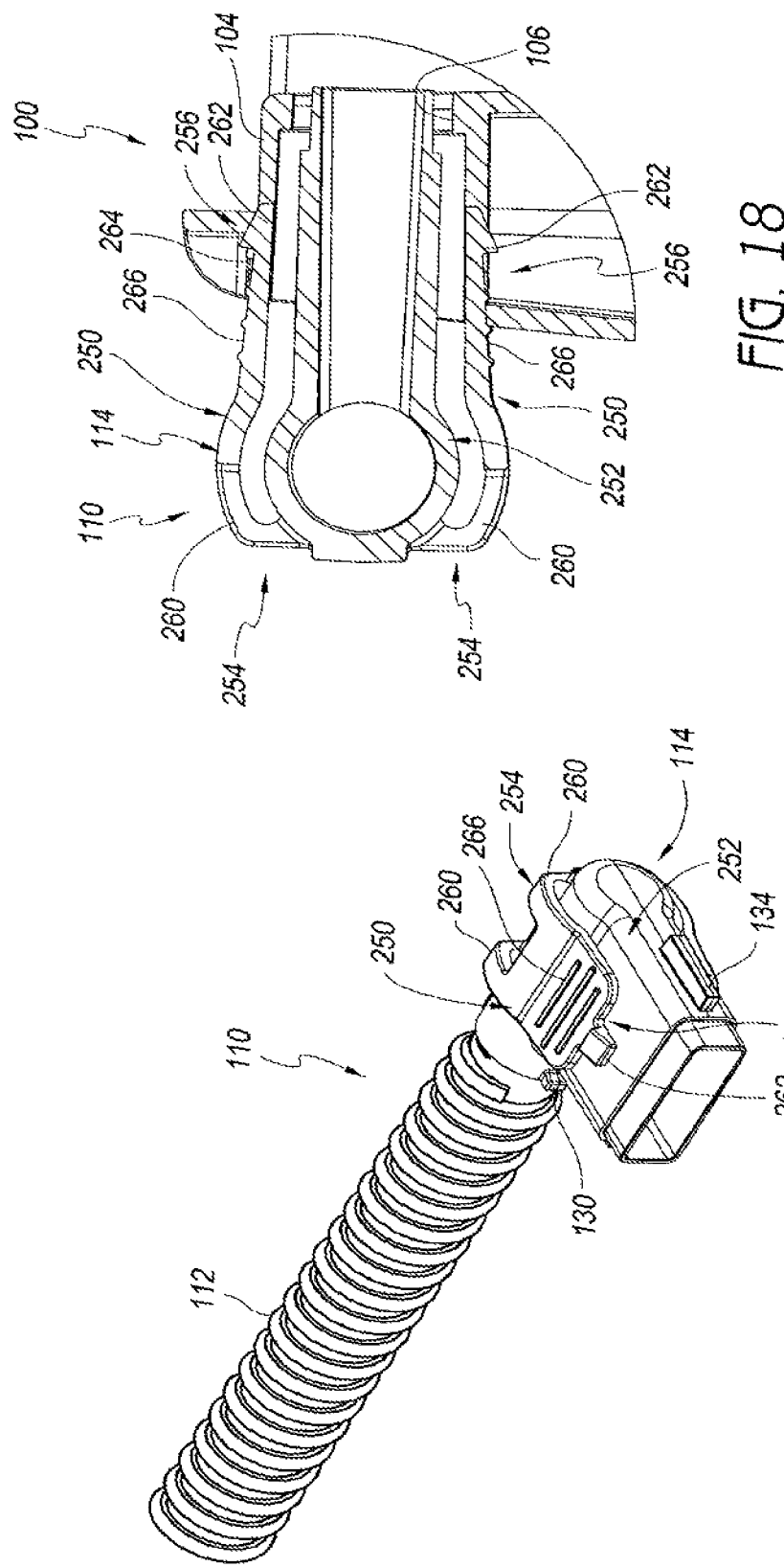

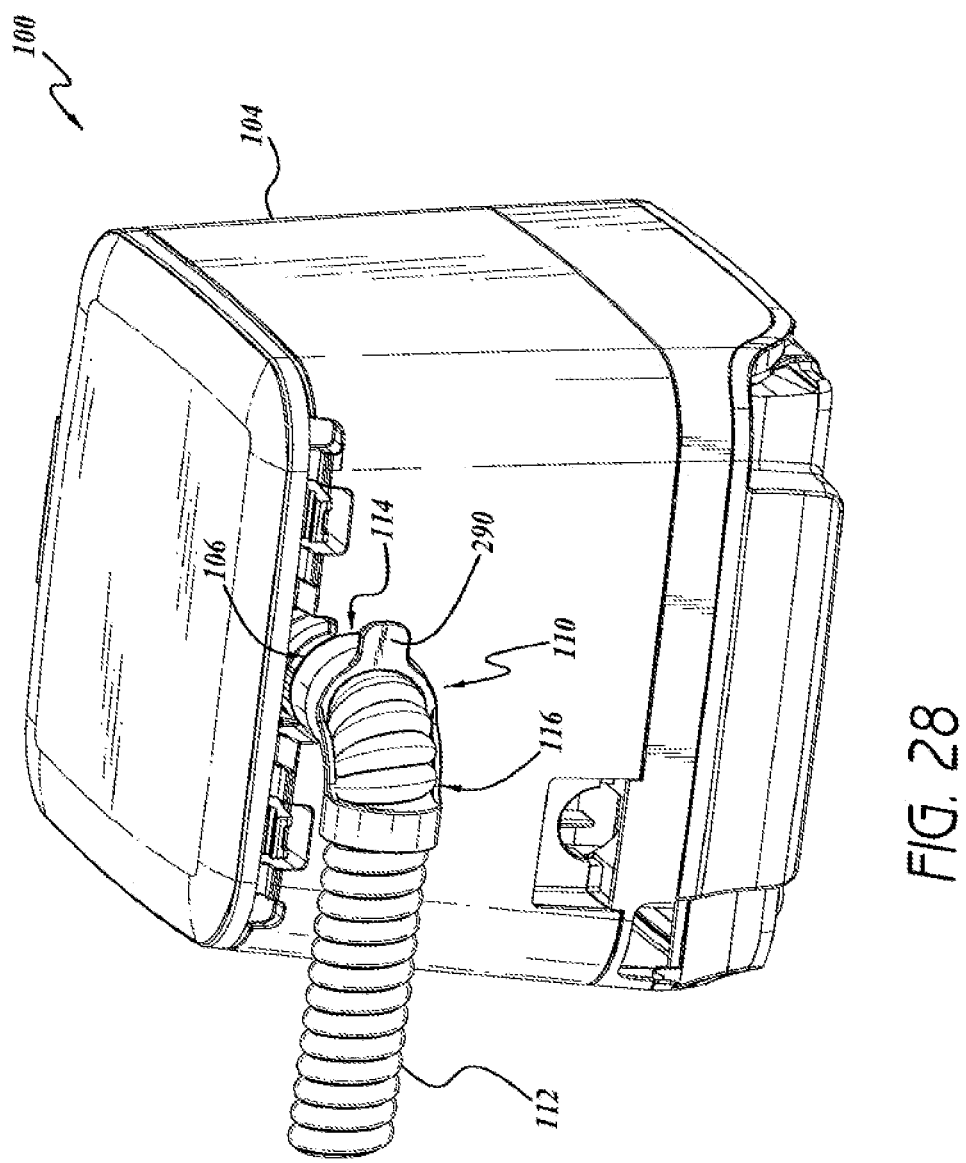

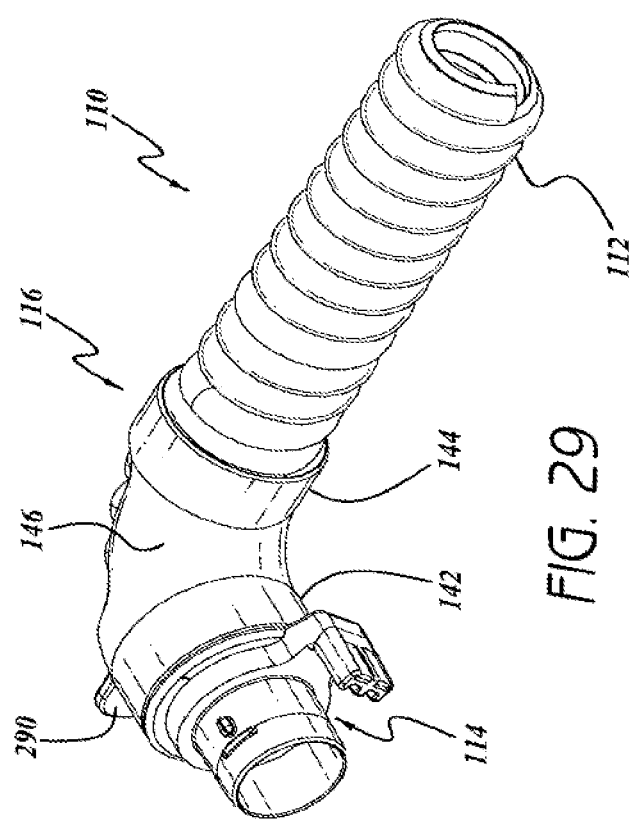
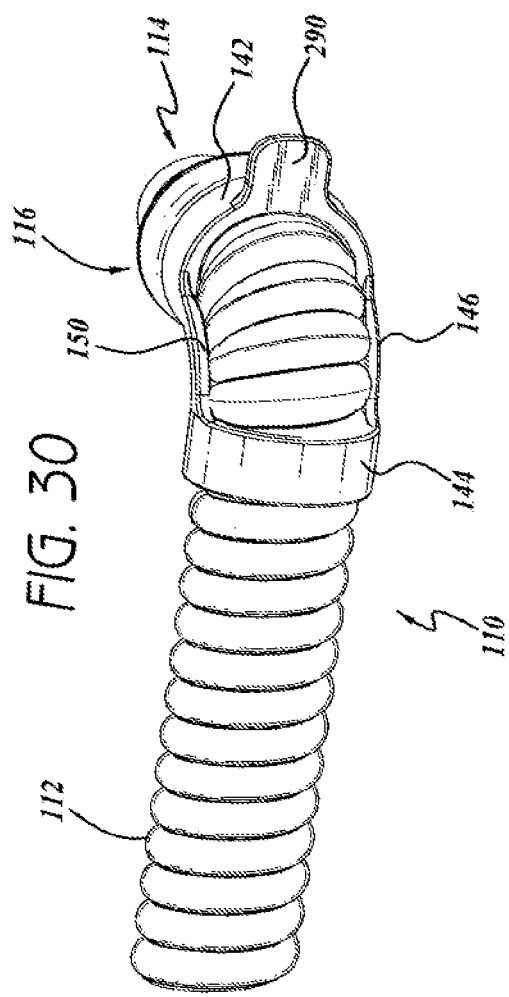

BREATHING TUBE ASSEMBLIES WITH ADJUSTABLE ELBOW

INCORPORATION BY REFERENCE TO ANY PRIORITY APPLICATIONS

This application is a continuation of U.S. patent application Ser. No. 14/420,241, filed Feb. 6, 2015, and titled "BREATHING TUBE ASSEMBLIES WITH ADJUSTABLE ELBOW," now U.S. Pat. No. 10,456,547, which application is a national stage entry of International Application No. PCT/NZ2013/000138, filed Aug. 8, 2013, and titled "BREATHING TUBE ASSEMBLIES WITH ADJUSTABLE ELBOW," which application claims benefit of U.S. Provisional Patent Application No. 61/681,083, filed Aug. 8, 2012, and titled "BREATHING TUBE ASSEMBLES WITH ADJUSTABLE ELBOW." The entire disclosure of each of the above items is hereby made part of this specification as if set forth fully herein and incorporated by reference for all purposes, for all that it contains. Any and all applications for which a foreign or domestic priority claim is identified in the Application Data Sheet as filed with the present application are hereby incorporated by reference and made a part of the present disclosure.

BACKGROUND OF THE INVENTION

Field of the Invention

The present invention generally relates to respiratory therapy systems and breathing tube assemblies that can be used with respiratory therapy systems. In particular, the present invention relates to elbows for breathing tube assemblies that permit adjustment of the breathing tube assembly relative to an accompanying therapy device.

Description of the Related Art

Respiratory therapy systems and devices, including continuous positive airway pressure (CPAP) systems and devices, flow therapy systems and devices, and breathing tube assemblies for use with such devices are well-known in the art. In addition, breathing tube assemblies that permit adjustment of a position of the breathing tube relative to the respiratory therapy device are known in the art. However, existing adjustable breathing tube assemblies are often complex to manufacture, which results in a high cost and, often, a shorter service life than non-adjustable assemblies.

SUMMARY OF THE INVENTION

Accordingly, a need exists for respiratory therapy systems and breathing tube assemblies that address one or more shortcomings of the prior art. In particular, one or more embodiments of the invention provide for adjustment of the breathing tube assembly relative to the respiratory therapy device in an assembly that can be manufactured in a cost-effective manner and that provides a similar or increased service life relative to non-adjustable or prior art adjustable assemblies.

Respiratory therapy systems and breathing tube assemblies for use with respiratory therapy systems, such as a CPAP system, of the preferred embodiments include an elbow that permits adjustment of a position of the breathing tube assembly relative to the respiratory therapy device. In some arrangements, the breathing tube assembly includes a breathing tube and a swivel elbow. The breathing tube is rotationally fixed relative to the respiratory therapy device and the swivel elbow rotatable relative to the breathing tube. In other arrangements, the breathing tube assembly includes an elbow that can be coupled to the respiratory therapy device in one of several possible positions.

A preferred embodiment involves a respiratory therapy system including a flow generator, a flexible breathing tube assembly, a patient interface and a swivel elbow. The flow generator generates a flow of a breathing gas and includes an outlet for the flow of the breathing gas. The flexible breathing tube assembly includes a connector and a tube, which has a first end and a second end. The first end is coupled to the connector in a substantially non-rotatable manner. The connector couples the breathing tube to the outlet of the flow generator. The patient interface is coupled to the second end of the breathing tube such that the breathing tube can deliver the flow of the breathing gas from the flow generator to the patient interface. The swivel elbow is rotatably coupled to the connector of the breathing tube. The swivel elbow includes an engagement portion that at least partially surrounds the breathing tube to couple the swivel elbow to the breathing tube. The swivel elbow further includes a curved surface portion that guides a first portion of the breathing tube into a curved shape. The breathing tube is rotatable relative to the engagement portion of the swivel elbow such that the swivel elbow can be rotated relative to the connector to vary a direction in the breathing tube extends relative to the flow generator.

In some arrangements, the swivel elbow has a greater resistance to deformation than the breathing tube such that, in use, the swivel elbow inhibits occlusion of the breathing tube as a result of being collapsed by external forces. The engagement portion can completely surround the breathing tube. The engagement portion can only partially surround the breathing tube thereby defining a slit in the engagement portion.

In some arrangements, the curved surface portion extends between a portion of the swivel elbow that is coupled to the connector and the engagement portion. The curved surface portion can subtend an angle of approximately 90 degrees in a length direction of the breathing tube. The curved surface portion can surround approximately one-half of the breathing tube in a circumferential direction. The curved surface portion can be located on an inside portion or an outside portion of the curved shape. The swivel elbow can also include a tab sized and shaped to facilitate grasping by a user. The tab can be located generally opposite the curved surface portion or engagement portion. The swivel elbow can be constructed from a pair of interlocking halves.

In some arrangements, the connector includes a first interference surface portion and the flow generator includes a second interference surface portion that, when the breathing tube is coupled to the flow generator, engages the first interference surface portion to secure the breathing tube to the flow generator. The second interference surface portion can be defined by the outlet of the flow generator and the first interference surface portion can be defined by a portion of the connector that is received within the outlet. The second interference surface portion can be adjacent the outlet of the flow generator and the first interference surface portion can be defined by a portion of the connector that is adjacent the outlet. The first interference surface portion can be defined by a tab of the connector that engages a corresponding recess of the flow generator. The second interference surface portion can be defined by at least one tab of the flow generator, which engages an external shoulder of the swivel elbow, which defines the first interference surface portion.

In some arrangements, the connector includes a first electrical terminal configured to connect to a second electrical terminal on the flow generator. The first and second electrical terminals can connect a heat source of the flow generator to a heating coil of the breathing tube. The first and second electrical terminals can alternatively or additionally provide for data communication between the breathing tube and the flow generator.

An embodiment involves a breathing tube assembly, which includes a flexible breathing tube that can be coupled to a flow generator to receive a flow of breathing gas from the flow generator and can be coupled to a patient interface to deliver the flow of the breathing gas to the patient interface. A swivel elbow engages a portion of the breathing tube. The swivel elbow includes a curved surface portion that guides the portion of the breathing tube into a curved shape. The swivel elbow is rotatable relative to the flow generator and is also rotatable relative to the portion of the breathing tube such that the swivel elbow can be rotated relative to the flow generator to vary a direction in which the breathing tube extends relative to the flow generator.

In some arrangements, the curved surface portion of the swivel elbow contacts an external surface of the breathing tube. The curved surface portion can subtend an angle of approximately 90 degrees in a length direction of the breathing tube. The curved surface portion can surround approximately one-half of the breathing tube in a circumferential direction. The curved surface portion can be located on an inside portion or an outside portion of the curved shape. The swivel elbow can also include a tab sized and shaped to facilitate grasping by a user. The tab can be located generally opposite the curved surface portion or a portion of the swivel elbow that at least partially surrounds the breathing tube. The swivel elbow can be constructed from a pair of interlocking halves.

In some arrangements, the connector includes a first interference surface portion and the flow generator comprises a second interference surface portion that, when the breathing tube is coupled to the flow generator, engages the first interference surface portion to secure the breathing tube to the flow generator. The second interference surface portion can be defined by the outlet of the flow generator and the first interference surface portion can be defined by a portion of the connector that is received within the outlet. The second interference surface portion can be adjacent the outlet of the flow generator and the first interference surface portion can be defined by a portion of the connector that is adjacent the outlet. The first interference surface portion can be defined by a tab of the connector that engages a corresponding recess of the flow generator. The second interference surface portion can be defined by at least one tab of the flow generator, which engages an external shoulder of the swivel elbow, which defines the first interference surface portion.

In some arrangements, the connector includes a first electrical terminal configured to connect to a second electrical terminal on the flow generator. The first and second electrical terminals can connect a heat source of the flow generator to a heating coil of the breathing tube. The first and second electrical terminals can alternatively or additionally provide for data communication between the breathing tube and the flow generator.

An embodiment involves a respiratory therapy system, including a flow generator, a flexible breathing tube assembly and a patient interface. The flow generator generates a flow of a breathing gas and includes an outlet for the flow of the breathing gas. The flow generator also includes a first electrical terminal and a second electrical terminal. The flexible breathing tube assembly includes a tube and a connector. The tube has a first end and a second end. The first end of the tube is coupled to the connector. The connector couples the breathing tube assembly to the outlet of the flow generator. The connector has a tube electrical terminal that is connectable to either of the first electrical terminal or the second electrical terminal of the flow generator. The patient interface is coupled to the second end of the tube such that the breathing tube assembly can deliver the flow of the breathing gas from the flow generator to the patient interface. The breathing tube assembly can be connected to the flow generator in a first position in which the tube electrical terminal is coupled to the first electrical terminal of the flow generator, and can be connected to the flow generator in a second position in which the tube electrical terminal is coupled to the second electrical terminal of the flow generator.

In some arrangements, the outlet of the flow generator defines an outlet axis and the first end of the tube defines a tube axis, and the connector orients the tube axis at an angle relative to the outlet axis in each of the first position and the second position. The angle can be approximately 90 degrees. The tube can extend in a first direction when the breathing tube assembly is in the first position and can extend in a second direction when the breathing tube assembly is in the second position, wherein the second position is opposite the first direction.

In some arrangements, the connector includes a first interference surface portion and the flow generator comprises a second interference surface portion that, when the breathing tube is coupled to the flow generator, engages the first interference surface portion to secure the breathing tube to the flow generator. The second interference surface portion can be defined by the outlet of the flow generator and the first interference surface portion can be defined by a portion of the connector that is received within the outlet. The first interference surface portion can be defined by a tab of the connector that engages a corresponding recess of the flow generator.

In some arrangements, the first and second electrical terminals and the tube electrical terminal connect a heat source of the flow generator to a heating coil of the breathing tube. The first and second electrical terminals and the tube electrical terminal can additionally or alternatively provide for data communication between the breathing tube and the flow generator.

BRIEF DESCRIPTION OF THE DRAWINGS

These and other features, aspects and advantages of the breathing tube assembly with elbow are disclosed herein with reference to drawings of preferred embodiments, which are provided for the purpose of illustration and not limitation. The drawings contain thirty (30) figures.

FIG. 6 is a perspective view of the breathing tube assembly of FIG. 5 separated from the flow generator.

FIG. 7 is a perspective view of the breathing tube assembly of FIG. 6, with the swivel elbow separated from the tube and the connector.

FIG. 8 is a sectional view of the flow generator and breathing tube assembly of FIG. 5 taken along the line 8-8 of FIG. 5.

FIG. 10 is a perspective view of the breathing tube assembly of FIG. 9 separated from the flow generator.

FIG. 11 is a perspective view of the breathing tube assembly of FIG. 10, with the swivel elbow separated from the tube and the connector.

FIG. 12 is a sectional view of the flow generator and breathing tube assembly of FIG. 9 taken along the line 12-12 of FIG. 9.

FIG. 17 is a perspective view of the breathing tube assembly of FIG. 16 separated from the flow generator.

FIG. 18 is a sectional view of the flow generator and breathing tube assembly of FIG. 16 taken along line 18-18 of FIG. 16.

FIG. 28 is a perspective view of a flow generator and an alternative breathing tube assembly, which is similar to the breathing tube assemblies of FIGS. 1-15. The breathing tube assembly of FIG. 28 includes a tube, a connector and a swivel elbow.

FIG. 29 is a perspective view of an inside of the breathing tube assembly of FIG. 28 separated from the flow generator.

FIG. 30 is a perspective view of an outside of the breathing tube assembly of FIG. 28 separated from the flow generator.

DETAILED DESCRIPTION OF THE PREFERRED EMBODIMENTS

The respiratory therapy systems, breathing tube assemblies and related components are described herein in the context of a healthcare respiratory device that provides a breathing gas at or above a minimum pressure or flow, which preferably is an elevated pressure relative to the ambient pressure. In particular, the illustrated respiratory therapy system is a continuous positive airway pressure (CPAP) device that provides a breathing gas (e.g., air) at or above a minimum pressure. The pressure level can be fixed or variable. Examples of suitable CPAP devices include the ICON™ Series or SleepStyle™ Series CPAP devices sold by Fisher & Paykel Healthcare. However, the disclosed systems, breathing tube assemblies and related components can also be utilized in other contexts or applications, as well. For example, the systems, breathing tube assemblies and related components can be utilized in adult, pediatric or infant respiratory systems and surgical humidification systems, among others. Therefore, the use of the terms "humidifier," "humidification device," or "CPAP device" herein are intended to cover other types of flow generators (humidified or non-humidified), as well.

Figure 1:
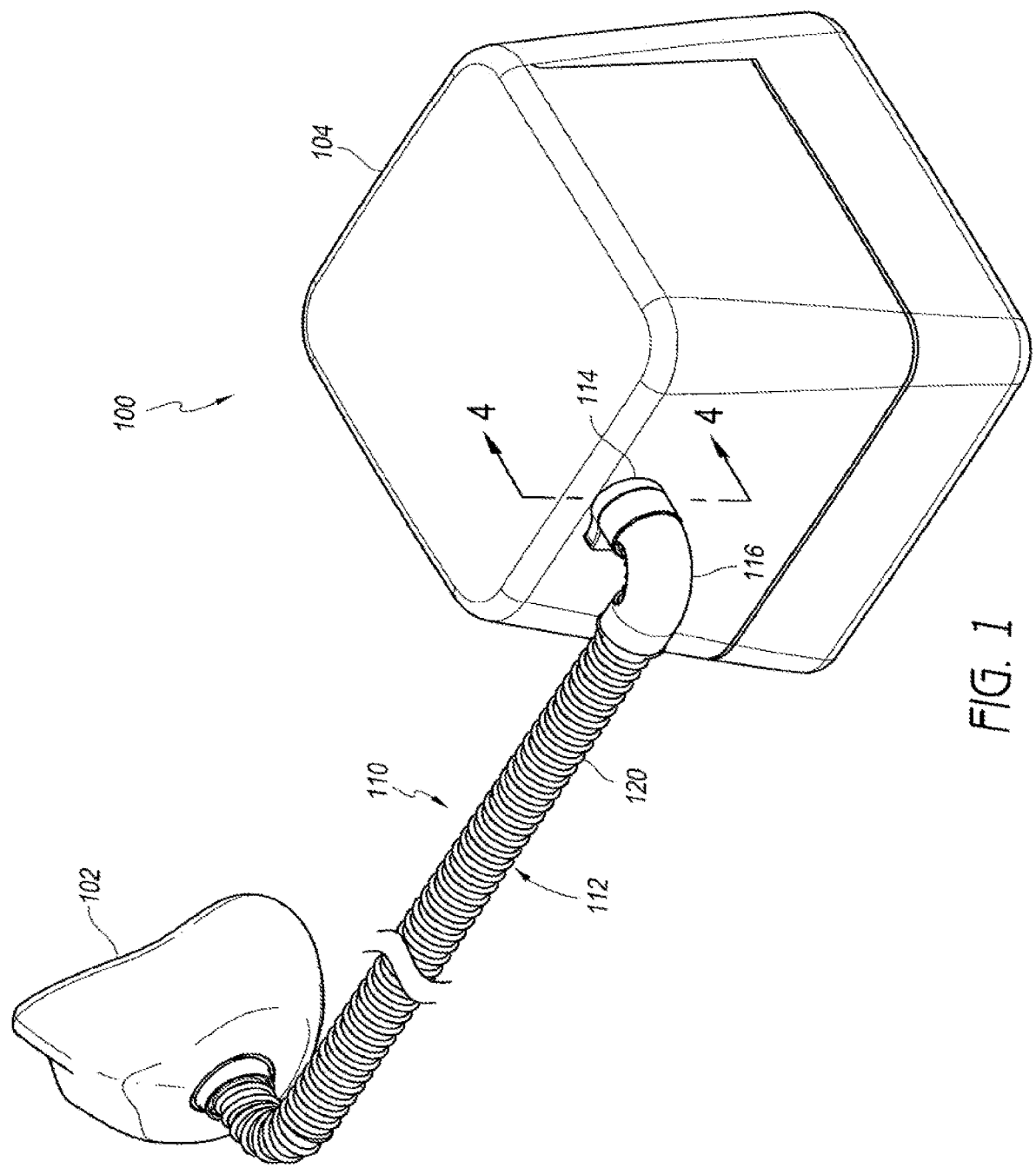
FIG. 1 is a perspective view of a flow generator and a breathing tube assembly, which includes a tube, a connector and a swivel elbow.
Figure 4:
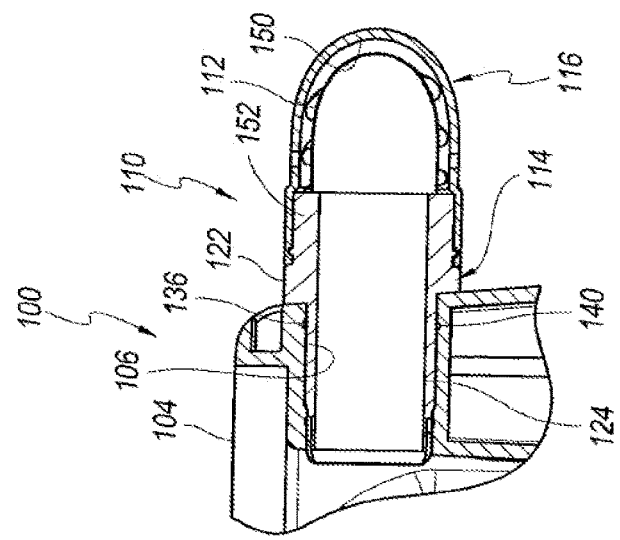
FIG. 4 is a sectional view of the flow generator and breathing tube assembly of FIG. 1 taken along the line 4-4 of FIG. 1.
Figure 2:
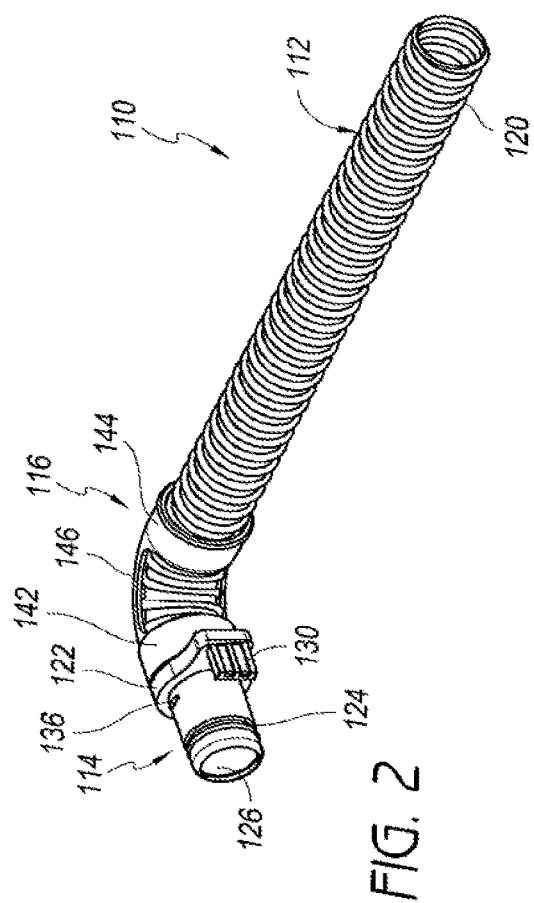
FIG. 2 is a perspective view of the breathing tube assembly of FIG. 1 separated from the flow generator.
Figure 3:
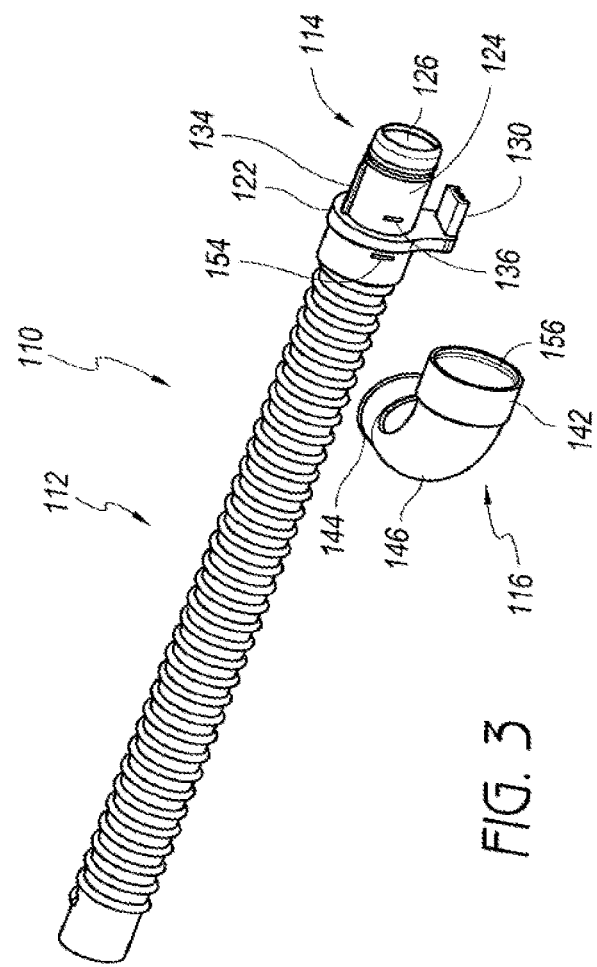
FIG. 3 is a perspective view of the breathing tube assembly of FIG. 2, with the swivel elbow separated from the tube and the connector.
Figure 5:
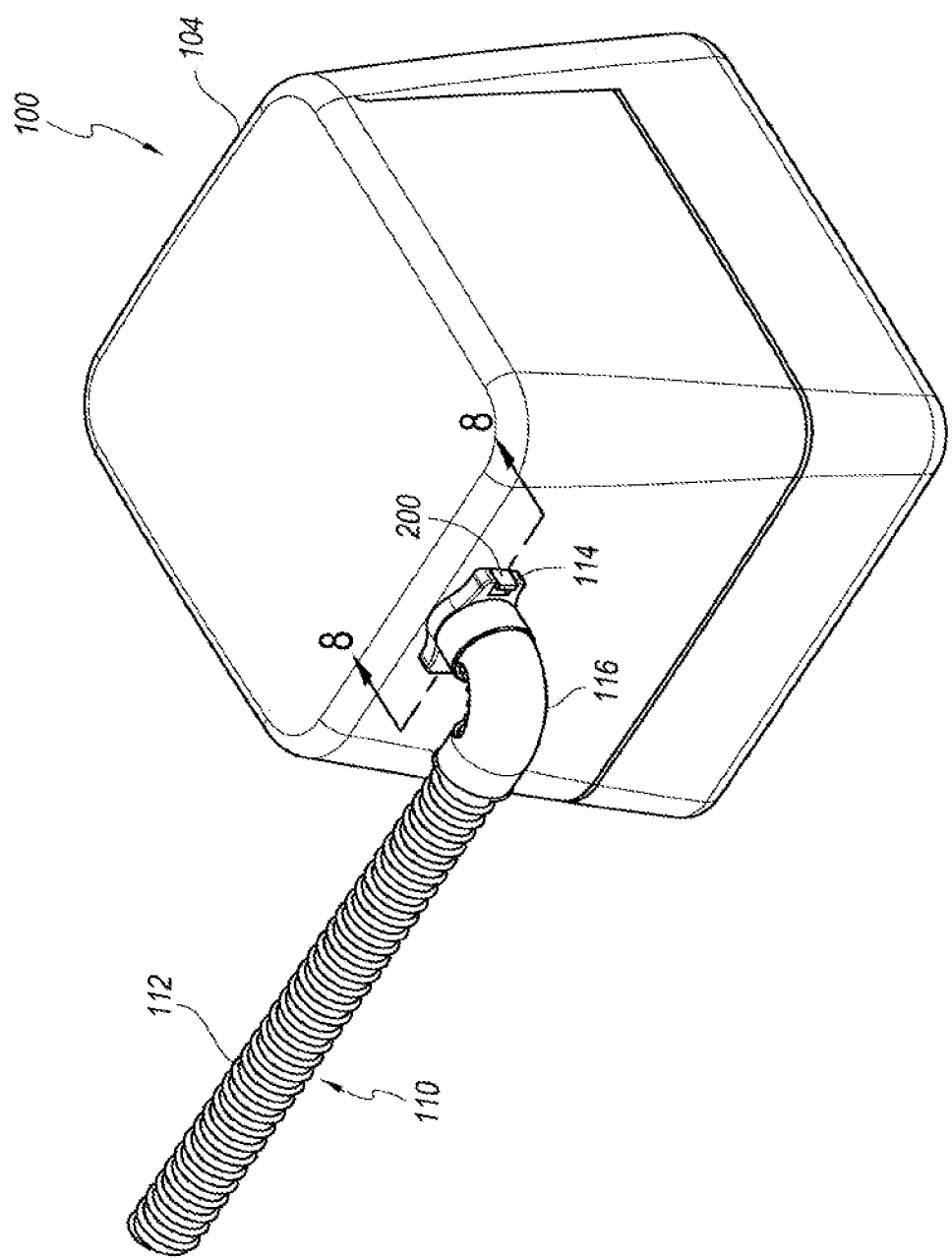
FIG. 5 is a perspective view of a flow generator and an alternative breathing tube assembly, which includes a tube, a connector and a swivel elbow.
Figure 9:
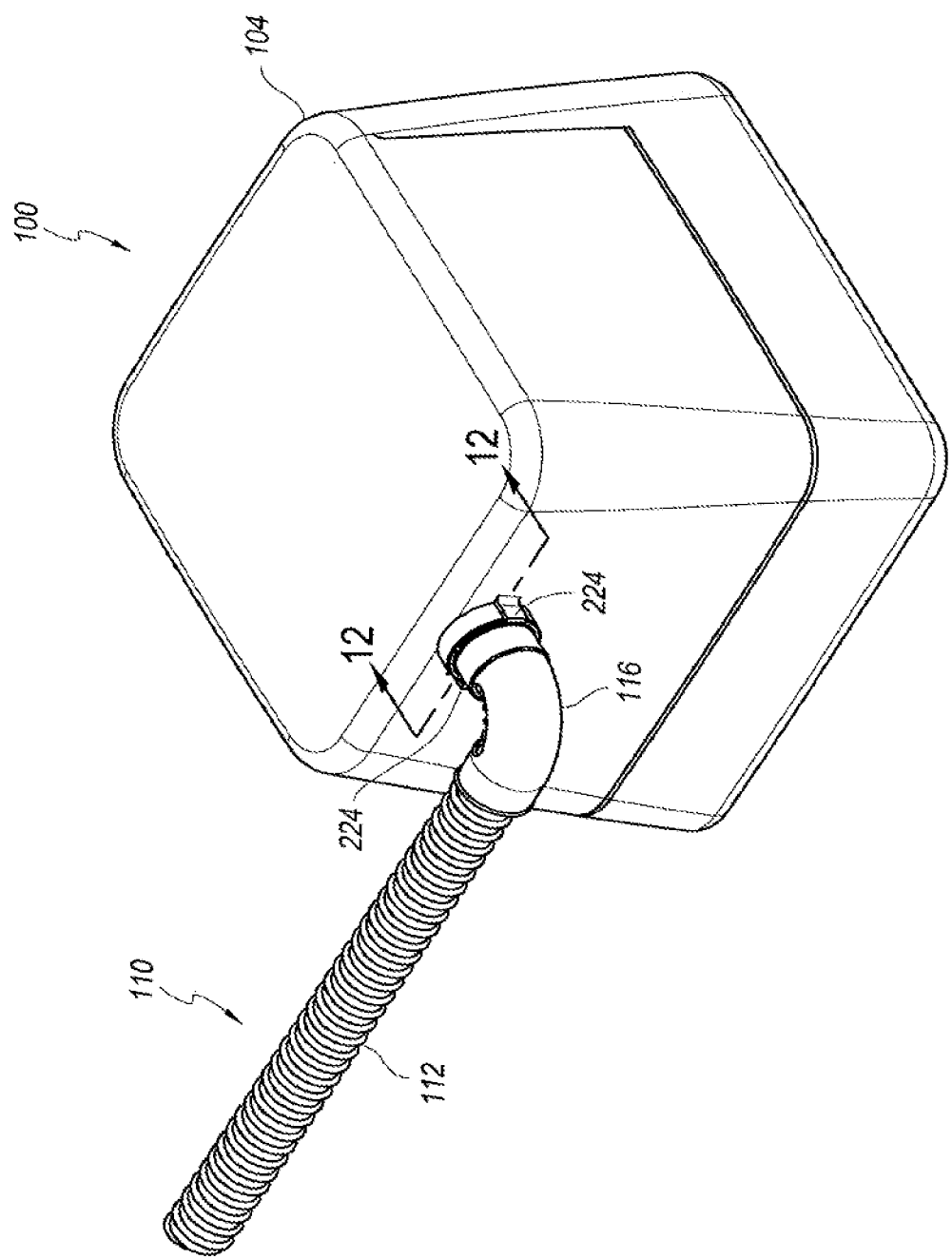
FIG. 9 is a perspective view of a flow generator and yet another alternative breathing tube assembly, which includes a tube, a connector and a swivel elbow.

FIGS. 1-4 illustrate a respiratory therapy system 100, which preferably provides a flow of a breathing gas (e.g., air) at a positive pressure to a patient interface 102 to, among other uses, treat obstructive sleep apnea. The system 100 includes a flow generator 104, which, as described above, preferably is a CPAP device that generates a flow of humidified breathing gas, such as air. The CPAP device 104 preferably includes an internal water reservoir (not shown), a heating device that heats the water in the water reservoir, and a blower or pump (not shown) that generates a flow of air. The flow of air is passed through the water reservoir to increase the humidity of the flow of air and the humidified flow of air is delivered to an outlet 106 (FIG. 4). In other arrangements, the flow generator 104 could provide a flow of non-humidified breathing gas, which could be air or another suitable gas.

A conduit or breathing tube assembly 110 is coupled to the outlet 106 at one end and is coupled to the patient interface 102 at the other end to deliver the humidified flow of air to from the outlet 106 to the patient interface 102. The patient interface 102 can be any suitable type of interface that can deliver the flow of air to the respiratory system of the patient. The illustrated patient interface 102 is a nasal mask, which covers the nose of a patient, but does not cover the patient's mouth. Other suitable patient interfaces include, for example and without limitation, full face masks, nasal cannula, endotracheal or tracheostomy interfaces.

The breathing tube assembly 110 preferably includes a tube portion or tube 112, a connector 114 and a swivel elbow 116. The tube 112 is a flexible tube to provide for freedom of movement of the patient interface 102 relative to the CPAP device 104. That is, preferably, the tube 112 is capable of bending along its length without a significant amount of resistance so as to accommodate movement of a user of the system 100 within a range of motion of the breathing tube assembly 110. The tube 112 can be connectable to the patient interface 102 by any suitable arrangement, such as an interlocking or friction-fit arrangement, for example and without limitation. Preferably, the tube 112 includes an integrated electrical element or circuit 120, which can be a heating circuit or heating coil, a data circuit, any other type of electrical element or circuit, or any combination thereof. In the illustrated tube 112, the electrical element 120 is a spiral-wound heating coil that is enclosed within a wall of the tube 112.

The connector 114 is coupled to the end of the tube 112 opposite the patient interface 102 and permits the breathing tube assembly 110 to be connected to the CPAP device 104. The connector 114 can be coupled to the end of the tube 112 in any suitable manner to create an airtight or substantially airtight connection therebetween. The connector 114 preferably is permanently coupled to the tube 112, but could also be removable coupled to the tube 112, if desired. The connector 114 is configured to be received within the outlet 106 of the CPAP device 104. In particular, preferably, the connector 114 includes a flange portion or flange 122 and a shaft portion or shaft 124 that extends from the flange 122 in a direction opposite the tube 112. The shaft 124 is hollow and defines an internal passage 126 that communicates with the interior passage of the tube 112. In the illustrated arrangement, the shaft 124 of the connector 114 is received within the outlet 106 of the CPAP device 104; however, in other arrangements, the connector 114 could define a female portion of the connection and the outlet 106 could define the male portion.

Preferably, the flange 122 abuts against an exterior surface of the CPAP device 104 when the breathing tube assembly 110 is assembled to the CPAP device 104. The flange 122 also carries an electrical terminal, which engages a complementary electrical terminal of the CPAP device 104 to permit electrical signals or electrical energy to be transmitted between the CPAP device 104 and the breathing tube assembly 110. In the illustrated arrangement, the electrical terminal of the connector 114 is a plug 130 and the electrical terminal of the CPAP device 104 is a receptacle or port 132 (FIG. 8). However, this arrangement could also be reversed, if desired. The plug 130 is electrically connected to the heating coil 120 and/or other electrical element of the breathing tube assembly 110. The port 132 is electrically connected to the heating circuit and/or other electrical circuits of the CPAP device 104. Preferably, the heating circuit of the CPAP device 104 provides electrical energy to the heating coil 120 of the breathing tube assembly 110 so that the heating coil 120 can provide heat energy to the flow of humidified air passing through the breathing tube assembly 110. As is known, such an arrangement can prevent or limit condensation within the breathing tube assembly 110. In addition, or in the alternative, the plug 130 and port 132 could provide for other electrical signals, such as data signals, to be communicated between the CPAP device 104 and the breathing tube assembly 110. For example, a sensor at the patient interface-end of the breathing tube assembly 110 could provide data regarding one or more parameters of the flow of air (e.g., temperature, humidity level) for use by the control system of the CPAP machine. Any other desirable electrical signals could also be transmitted.

Preferably, the connector 114 includes features to facilitate the insertion of the connector 114 into and/or retention of the connector 114 within the outlet 106 of the CPAP device 104. For example, the shaft 124 of the connector 114 can include a guide rib 134, which extends in a lengthwise direction of the shaft 124. The guide rib 134 can engage with a complementary groove (not shown) of the outlet 106 to assist in the insertion of the connector 114 into the outlet 106 with a proper alignment of the plug 130 and port 132. In addition to, or in the alternative of, the guide rib 134, the plug 130 could be increased in length relative to the illustrated arrangement of FIGS. 1-4. For example, the plug 130 could be between about ¾ of the length of the shaft 124 to about the same length or longer than the shaft 124. In such an arrangement, the plug 130 would engage the port 132 sooner and assist in the proper alignment and insertion of the connector 114 into the outlet 106. In the illustrated arrangement, the guide rib 134 is located opposite the plug 130.

The connector 114 preferably also includes a feature that facilitates retention of the connector 114 to the CPAP device 104. In some arrangements, the feature is an interlocking arrangement between the connector 114 and the CPAP device 104. In the illustrated arrangement, the shaft 124 includes a protrusion 136, which defines an interference or interlocking surface. The outlet 106 includes a complementary recess 140, which also defines an interference or interlocking surface. When the connector 114 is coupled to the CPAP device 104, the protrusion 136 is received within the recess 140 and the interaction between their respective interference surfaces creates a retention force tending to inhibit undesired disconnection of the connector 114 from the CPAP device 104. In some arrangements, the location of the protrusion 136 and recess 140 could be reversed. The illustrated protrusion 136 and recess 138 are elongated and extend in a circumferential direction of the shaft 124 and outlet 106, respectively. In addition, preferably, more than one protrusion/recess pair 136/140 is provided. In the illustrated arrangement, two pairs of corresponding protrusions 136 and recesses 140 are provided and are equally spaced around the circumference of the shaft 124. Although a protrusion 136 and recess 140 arrangement are preferred, other suitable types of interlocking or interference arrangements could also be used.

Preferably, the breathing tube assembly 110 includes one or more features that orients a portion of the breathing tube 112 into a bend and/or provides crush protection to a portion of the breathing tube 112. Preferably, the breathing tube 112 can also be moved relative to the CPAP device 104 such that the breathing tube 112 can be oriented in at least two different positions and preferably to any position within a range of possible positions. In some arrangements, the portion of the breathing tube 112 that is oriented into a bend and/or provided crush protection is a portion of the tube 112 adjacent the connector 114. In some cases, the outlet 106 is positioned on a rearward surface of the CPAP device 104 (e.g., relative to a user interface or otherwise-defined forward surface). Therefore, it is often desirable for the breathing tube 112 to bend at or near the connector 114/outlet 106 to reduce the amount of room necessary at the outlet-side (e.g., rearward surface) of the CPAP device 104 to accommodate the breathing tube 112. In addition, the rearward (or other) positioning of the outlet 106 can create a risk that the CPAP device 104 is pushed toward a wall or other object until the breathing tube 112 is crushed against the wall or object, which could cause a partial or total occlusion of the breathing tube 112 and/or cause damage to the breathing tube 112. Thus, it is often desirable to provide for some amount of protection to the breathing tube 112 and especially a portion of the breathing tube 112 at or near the outlet 106. The CPAP device 104 can also be located on either side of the patient/user. Therefore, it is often also desirable to permit the breathing tube 112 to be adjustable (e.g., rotatable) relative to the CPAP device 104. In the illustrated arrangement, the swivel elbow 116 provides each of the above-described features. That is, the illustrated swivel elbow 116 urges the tube 112 into a bend, provides crush protection and permits the position of the tube 112 to be varied relative to the CPAP device 104. However, in other arrangements, the swivel elbow 116 could provide less than all of these features. For example, the swivel elbow 116 could provide any one or combination of the above-described features.

Preferably, the swivel elbow 116 urges, guides, constrains or otherwise directs a portion of the tube 112 into a bend or a curved orientation. Preferably, the curved portion of the tube 112 is near or adjacent the connector 114. The illustrated swivel elbow 116 includes a first portion or connector engagement portion 142 that contacts, and preferably engages, the connector 114. The swivel elbow 116 also includes a second portion or tube engagement portion 144 that contacts, and preferably engages, the tube 112. In the illustrated arrangement, the connector engagement portion 142 and the tube engagement portion 144 are in the form of bands that substantially or entirely surround a circumference of the connector 114 and/or tube 112. In alternative arrangements, the swivel elbow 116 could instead be coupled to the CPAP device 104 while retaining some or all of the functions described herein.

The swivel elbow 116 further includes a tube guide portion 146 that extends between the connector engagement portion 142 and the tube engagement portion 144. Preferably, the tube guide portion 146 defines a curved surface 150, which guides the tube 112 into a curved orientation. Accordingly, an axis of the connector engagement portion 142 is offset at an angle relative to an axis of the tube engagement portion 144. In the illustrated arrangement, the angle is approximately 90 degrees. However, in other arrangements, the angle could be any angle within the range of between about 45 degrees and about 180 degrees. If desired, the angle could also be outside of this range. In some arrangements, the angle could be adjustable by, for example, providing a pivot in the swivel elbow 116. Preferably, at least a portion of the curved surface 150 contacts the tube 112; however, the tube guide portion 146 could also be configured to simply interconnect the connector engagement portion 142 and the tube engagement portion 144, which could orient the tube 112 into a bend with little or no contact between the tube 112 and the tube guide portion 146. In addition, although the connector engagement portion 142, the tube engagement portion 144 and the tube guide portion 146 are external of the tube 112, in alternative arrangements one or more of these structures could be internal to the tube 112.

Preferably, the swivel elbow 116 also provides at least some amount of crush protection to the tube 112. Therefore, preferably, the swivel elbow 116, or at least the tube guide portion 146, is constructed from a material that is more rigid than the tube 112 or has greater resistance to bending relative to the tube 112. Relatively rigid plastic, metal or other materials can be used, although one preferred embodiment is constructed from plastic. Preferably, the tube guide portion 146 can maintain its shape in response to expected crushing forces in normal use of the system 100. The tube guide portion 146 can completely surround a circumference of the tube 112; however, in the illustrated arrangement, the tube guide portion 146 only partially surrounds the tube 112. In particular, the illustrated tube guide portion 146 surrounds approximately or exactly half of the circumference of the tube 112. Preferably, the tube guide portion 146 is positioned on the outer side of the tube 112 relative to the bend (e.g., the center point of the bend radius) such that the tube guide portion 146 is positioned to contact a wall or other object instead of the tube 112, thereby reducing the likelihood of partial or complete occlusion of the tube 112. As described above, the tube guide portion 146 could be internal or external of the tube 112.

Preferably, the swivel elbow 116 is rotatable about at least the longitudinal axis of the outlet 106 of the CPAP device 104 to permit a position of the tube 112 to be varied relative to the CPAP device 104. In the illustrated arrangement, the swivel elbow 116 can be rotated 360 degrees about the axis of the outlet 106, and beyond. That is, the swivel elbow 116 can be rotated in a single direction for multiple rotations. However, in other arrangements, the rotation of the swivel elbow 116 may be limited, either as a result of the elbow 116 structure or as a result of interference with other components/objects. For example, rotation of the swivel elbow 116 can be less than 45 degrees, equal to or greater than 45 degrees, equal to or greater than 180 degrees, or equal to or greater than 270 degrees, among other possibilities.

As described above, the swivel elbow 116 can be coupled to the connector 114. In the illustrated arrangement, the connector engagement portion 142 receives a boss 152 of the connector 114, which extends from the flange 122 in the opposite direction of the shaft 124. However, this arrangement could be reversed and the connector engagement portion 142 could be received within the boss 152, among other possible connection arrangements. Preferably, an interlocking arrangement secures the connector engagement portion 142 to the boss 152 in an axial direction, but permits rotation therebetween. The illustrated interlocking arrangement includes a circumferential protrusion 154 defined by one of the connector engagement portion 142 and the boss 152 and a complementary circumferential groove 156 defined by the other of the connector engagement portion 142 and the boss 152. In the illustrated arrangement, the protrusion 154 is defined by the boss 152 and the groove 156 is defined by the connector engagement portion 142; however, this arrangement could be reversed. In addition, the illustrated protrusion 154 is not continuous about the entire circumference of the boss 152. In particular, the illustrated protrusion 154 includes at least a pair, and preferably exactly a pair, of protrusion portions 154 equally spaced about the circumference of the boss 152. In addition, other types of interlocking arrangements can also be used.

Preferably, the swivel elbow 116 is not coupled to the tube 112 and does not tightly surround the tube 112 such that relative rotation between the swivel elbow 116 and the tube 112 is permitted. Preferably, the tube 112 is relatively loosely received within the swivel elbow 116 such that a gap exists or can exist upon centering of the tube 112 relative to the swivel elbow 116 to facilitate relative rotation therebetween. That is, the tube 112 preferably does not rotate relative to the outlet 106 of the CPAP device 104, but simply relies on the flexible nature of the tube 112 to change positions. In some arrangements, the gap between the tube 112 and the interior surface of the swivel elbow 116 can be within a range of about 0.05-0.1 millimeters. However, the gap could also be less than or greater than this ranges.

Because the swivel elbow 116 is capable of rotation relative to the connector 114, and the tube 112 can slide or rotate within the swivel elbow 116, adjustment of a position of the tube 112 relative to the CPAP device 104 is permitted, with the swivel elbow 116 being capable or directing the tube 112 in a desired direction. Advantageously, such an arrangement provides for adjustment of a position of the tube 112 relative to the CPAP device 104, while maintaining the electrical connection between the electrical terminals 130, 132, with a relatively simple structure that is cost-effective to manufacture and provides a long service life. In alternative arrangements, the swivel elbow 116 could provide for additional freedom of movement. For example, the swivel elbow 116 could be permitted to rotate about one or more axes that are perpendicular or substantially perpendicular to the axis of the outlet 106, shaft 124 and/or boss 152 (e.g., via a ball-and-socket joint).

In use, the CPAP device 104 can be set-up as normal, with the water reservoir filled (if applicable), the device 104 plugged in and mode or parameters of operation set appropriately. If necessary, the swivel elbow 116 can be assembled to the tube 112 and connector 114. For example, the swivel elbow 116 can be slid from the patient interface-end of the tube 112 to the connector-end of the tube 112 and coupled to the connector 114 via the interlocking arrangement. The patient interface 102 can be coupled to the tube 112 and the breathing tube assembly 110 can be coupled to the CPAP device 104 by coupling the connector 114 to the outlet 106. The swivel elbow 116 can be rotated (directly or indirectly through movement of the tube 112) to orient the tube 112 and the patient interface 102 in a desirable position relative to the CPAP device 104 (e.g., to the right, to the left, above or below), while maintaining connection between the electrical terminals 130, 132. The CPAP device 104 can then be used in accordance with a desired protocol.

FIGS. 5-8 illustrate another respiratory therapy system 100, including a breathing tube assembly 110, which are similar to the system 100 of FIGS. 1-4. Accordingly, the same reference numbers are used to indicate corresponding or similar components and only differences between the systems 100 will be described. Components, assemblies or features not specifically described can be assumed to be the same as or similar to the same component, assembly or feature of the system 100 of FIGS. 1-4.

In the system 100 of FIGS. 5-8, the connector 114 includes an alternative interlocking arrangement for securing the connector 114 to the CPAP device 104. In particular, in the illustrated interlocking arrangement, the flange 122 of the connector 114 includes a resilient tab 200 that engages a corresponding recess 202 of the CPAP device 104. Preferably, the tab 200 is located opposite the electrical plug 130; however, other positions are also possible. The tab 200 has a length that is about the same or somewhat longer than the length of the plug 130. Preferably, the tab 200 is shorter than the guide rib 134 (if present), which preferably is located halfway in between the tab 200 and the plug 130.

The tab 200 preferably is generally U-shaped and has a free end 204 and a fixed end 206 that is coupled to the flange 122 or other portion of the connector 114. Preferably, the tab 200 is unitary with the connector 114 and/or flange 122. The closed end of the U-shaped tab 200 preferably extends away from the flange 122 in the same direction as the shaft 124. An interference surface is defined by a protrusion 136 located on a leg of the U-shaped tab 200, which is the leg that defines the free end 204 in the illustrated arrangement. However, the protrusion 136 could be positioned on the other leg, or on both legs, in some arrangements. The free end 204 is movable such that the protrusion 134 can enter the recess 202 and then engage a corresponding interference surface defined by space, opening or recess 140 extending from the recess 202. In the illustrated arrangement, the interference surface is defined by the outer housing of the CPAP device 104 and the protrusion is received within a space behind the housing (interior of the CPAP device 104). The resiliency of the U-shaped tab 200 maintains contact between the interference surfaces until the free end 204 is moved to disengage the interference surfaces and permit disconnection of the connector 114 from the outlet 106. Preferably, the flange 122 defines a pair of prongs 210 that receive the tab 200 therebetween to provide protection to the tab 200 and inhibit out-of-plane movement of the tab 200. In other respects, the system 100 and breathing tube assembly 110 of FIGS. 5-8 is similar in structure and operation to the system 100 and tube assembly 110 of FIGS. 1-4.

FIGS. 9-12 illustrate another respiratory therapy system 100, including a breathing tube assembly 110, which are similar to the systems 100 of FIGS. 1-4 and 5-8. Accordingly, the same reference numbers are used to indicate corresponding or similar components and only differences between the systems 100 will be described. Components, assemblies or features not specifically described can be assumed to be the same as or similar to the same component, assembly or feature of the systems 100 of FIG. 1-4 or 5-8.

In the system 100 of FIGS. 9-12, an alternative interlocking arrangement is provided for securing the connector 114 to the CPAP device 104. In particular, in the illustrated interlocking arrangement, the swivel elbow 116 includes an annular portion 220 that surrounds all or a portion of the flange 122 of the connector 114. A transition between the connector engagement portion 142 and the annular portion 220 defines a shoulder 222 or interference surface. The CPAP device 104 includes at least one and preferably a pair of resilient tabs 224 that engage the annular portion 220 of the swivel elbow 116 to fix the connector 114 and swivel elbow 116 to the CPAP device 104 in an axial direction, but permit rotation between the swivel elbow 116 and the CPAP device 104. The connector 114 preferably is prevented from rotating relative to the CPAP device 104 by the plug 130 and/or other structures (e.g., guide rib 134). The tabs 224 include hook portions 226 that define interference surfaces that contact the interference surface(s) of the swivel elbow 116. In other respects, the system 100 and breathing tube assembly 110 of FIGS. 9-12 is similar in structure and operation to the systems 100 and tube assemblies 110 of FIG. 1-4 or 5-8.

Figure 15:
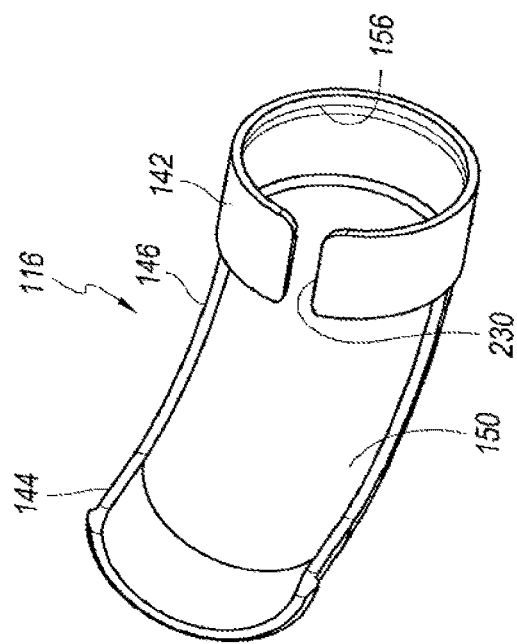
FIG. 15 is a perspective view of another alternative swivel elbow, which omits one of the loop end portions of the prior swivel elbows.
Figure 14:
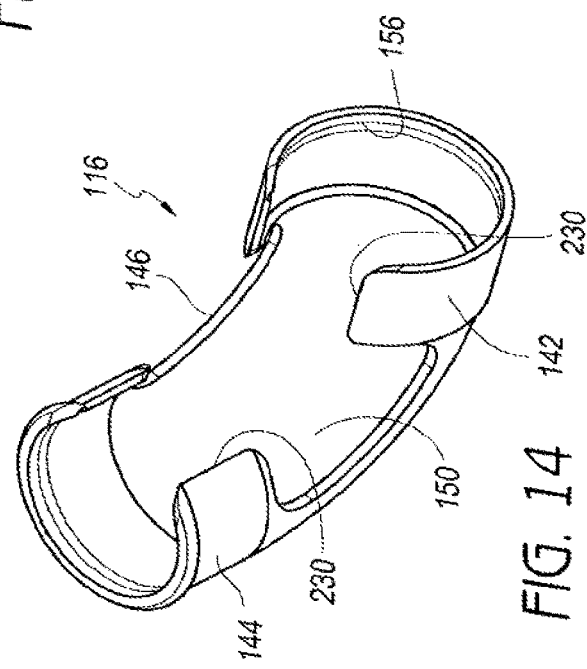
FIG. 14 is a perspective view of yet another alternative swivel elbow, which includes larger slits relative to the swivel elbow of FIG. 13.
Figure 13:
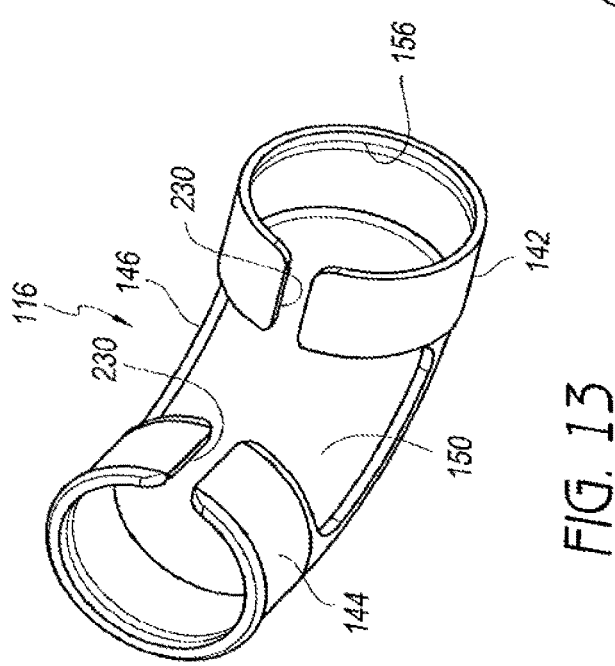
FIG. 13 is a perspective view of an alternative swivel elbow, which includes relatively small slits extending in a lengthwise direction at each end of the elbow.

FIGS. 13-15 illustrate swivel elbows 116 which are similar to the swivel elbows 116 of FIGS. 1-4, 5-8 and 9-12. Accordingly, the same reference numbers are used to indicate corresponding or similar components and only differences between the swivel elbows 116 will be described. Features not specifically described can be assumed to be the same as or similar to the same or corresponding feature of the swivel elbows 116 of FIG. 1-4, 5-8 or 9-12.

The swivel elbow 116 of FIG. 13 includes slits 230 in at least one of the connector engagement portion 142 or the tube engagement portion 144, and preferably includes a slit 230 in each. As a result, the portions 142 and/or 144 do not entirely surround a circumference of the connector 114 or tube 112 when assembled. Preferably, the slits 230 extend in a lengthwise direction entirely through the portions 142 and/or 144. The portions 142, 144 can be flexible enough to permit the connector 114 or tube 112 to be passed through the slit 230 when the portion 142, 144 is flexed outwardly. However, preferably, the flex provided by the portions 142, 144 is sufficient to simply ease assembly of the portion 142, 144 to the connector 114 or tube 112.

The swivel elbow 116 of FIG. 14 includes slits 230 that are wider or circumferentially longer than the slits 230 of the swivel elbow 116 of FIG. 13. The slits 230 of FIG. 14 can extend about ¼ or more of a circumference of the portions 142 and/or 144. Preferably, the slits 230 of the elbow 116 of FIG. 14 can permit the tube 112 or connector 114 to pass through the slits 230.

The swivel elbow 116 of FIG. 15 includes a truncated tube engagement portion 144. That is, the tube engagement portion 144 does not extend around the entire circumference of the tube 112 when assembled. Preferably, the tube engagement portion 144 is approximately coextensive in a circumferential direction with the tube guide portion 146. In some cases, this can be about one-half of the circumference of the tube 112. In other cases, this can be between about one-half and three-quarters of the circumference of the tube 112, or between about five-eighths and three-quarters of the circumference of the tube 112.

Any of the above-described swivel elbows 116 can be constructed of a single piece of material or multiple pieces of materials (the same or different material) connected together in any suitable manner. For example, in some cases, the elbow 116 is constructed from two halves, separated in a lengthwise direction and which can be coupled together (e.g., a clamshell arrangement). This can permit easy assembly onto the connector 114 and tube 112 without passing the entire tube 112 through the elbow 116.

FIGS. 16-27 illustrate alternative systems 100 including alternative connections between the breathing tube assembly 110 and the CPAP device 104. Accordingly, the same reference numbers are used to indicate corresponding or similar components and only differences between the systems 100 of FIGS. 16-27 and the prior systems will be described. Features not specifically described can be assumed to be the same as or similar to the same or corresponding feature of the systems of FIGS. 1-12.

In the systems of FIGS. 16-27, a fixed elbow connector 114 is provided to couple the tube 112 to the CPAP device 104. That is, in at least some arrangements, the elbow connectors 114 cannot rotate relative to the CPAP device 104 while remaining connected to the CPAP device 104. Instead, preferably, the elbow connectors 114 are configured to be connectable to the CPAP device 104 in at least two separate orientations or positions and provide electrical connection between the breathing tube assembly 110 and/or the patient interface 102 and the CPAP device 104 in each of the separate positions. In the illustrated arrangements, the CPAP device 104 includes two electrical terminals 132a and 132b, which may be in the form of electrical ports or receptacles. The connectors 114 include a single electrical terminal 130, which may be in the form of a plug and which can be connected to either of the electrical terminals 132a, 132b of the CPAP device 104. In other arrangements, these structures could be reversed and the ports could be provided on the connector 114 and the plug on the CPAP device 104. The arrangements of FIGS. 16-27 advantageously permits the breathing tube assembly 110 to be coupled to the CPAP device 104 in at least two positions that can selected based on the position of the user or patient relative to the CPAP device 104, while providing electrical connection in either position. In the illustrated arrangement, the positions are substantially opposite one another (i.e., tube 112 extending to the left and tube 112 extending to the right). In other arrangements, these positions can be varied to remain opposite one another (e.g., up and down) or to provide two options that are not opposite one another (e.g., horizontal and vertical). In addition, more than two options could be provided (e.g., left, right, up and down). In the illustrated arrangements, the connector 114 defines an angle of approximately or substantially 90 degrees between an axis of the breathing tube 112 (e.g., at the end coupled to the connector 114) and an axis of the outlet 106 of the CPAP device 104 to provide a relatively compact arrangement. However, in other arrangements, this angle could vary. The alternative connectors 114 of FIGS. 16-27 differ from one another primarily in the method of interconnecting the connector 114 with the CPAP device. Therefore, only the different interconnecting structures are described in detail below.

Figure 16:
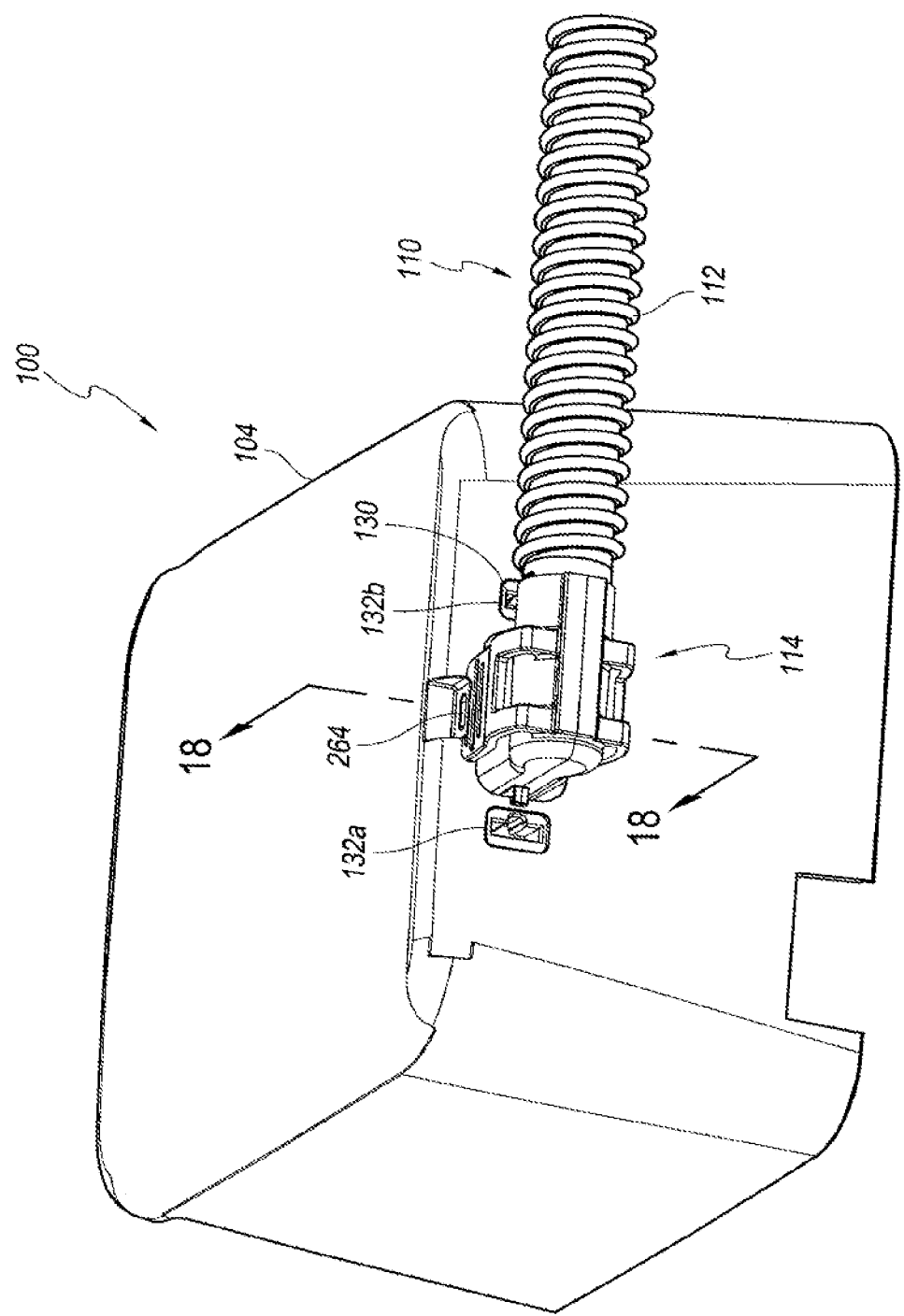
FIG. 16 is a perspective view of a flow generator and an alternative breathing tube assembly, which includes a tube and an elbow connector. The flow generator includes a first electrical terminal and a second electrical terminal. The breathing tube assembly includes a tube electrical terminal that connects to the first electrical terminal in a first position of the breathing tube assembly and connects to the second electrical terminal in a second position of the breathing tube assembly. The elbow connector includes an interlocking arrangement to selectively secure the breathing tube assembly to the flow generator.

In the arrangement of FIGS. 16-18, the connector 114 includes at least one, and preferably a pair, of resilient portions or resilient arms 250 that are movable relative to a main body 252 of the connector 114. Each arm 250 includes a fixed end 254 connected to the main body 252 and a movable end, which can be a free end 256 that is movable toward and away from the main body 252. The arms 250 are disposed on opposite sides of the main body 252. In the illustrated arrangement, the arms 250 are unitarily formed with the main body 252; however, in other arrangements the arms 250 could be separate members from the main body 252. Preferably, the arms 250 extend in a direction corresponding to an axis of the outlet 106 from the fixed end 254 to the free end 256 of the arms 250 and have a length that is equal to or greater than about one-half the length of the main body 252 of the connector 114.

The fixed end 254 of each arm 250 is in the form of a pair of spaced-apart connecting portions 260, which may provide a majority or all of the flexibility of the arms 250. The free end 256 of the arms 250 preferably includes a tab 262 that is configured to selectively engage a corresponding recess or opening 264 of the CPAP device 104 to secure the connector 114 (and breathing tube 112) to the CPAP device 104. The tab 262 and recess or opening 264 define cooperating interference surfaces that contact one another when the tab 262 is present in the recess or opening 264 to inhibit or prevent removal of the connector 114 from the CPAP device 104. In other arrangements, the location of the tab 262 and recess or opening 264 can be reversed, or other suitable interlocking structures can be provided. Preferably, the arms 250 also define finger grip portions 266, which may include ridges or other grip-enhancing features, that can be used to squeeze the arms 250 toward the main body 252 and toward one another (assuming a pair of arms 250) to release the tab 262 from the recess or opening 264.

Figure 19:
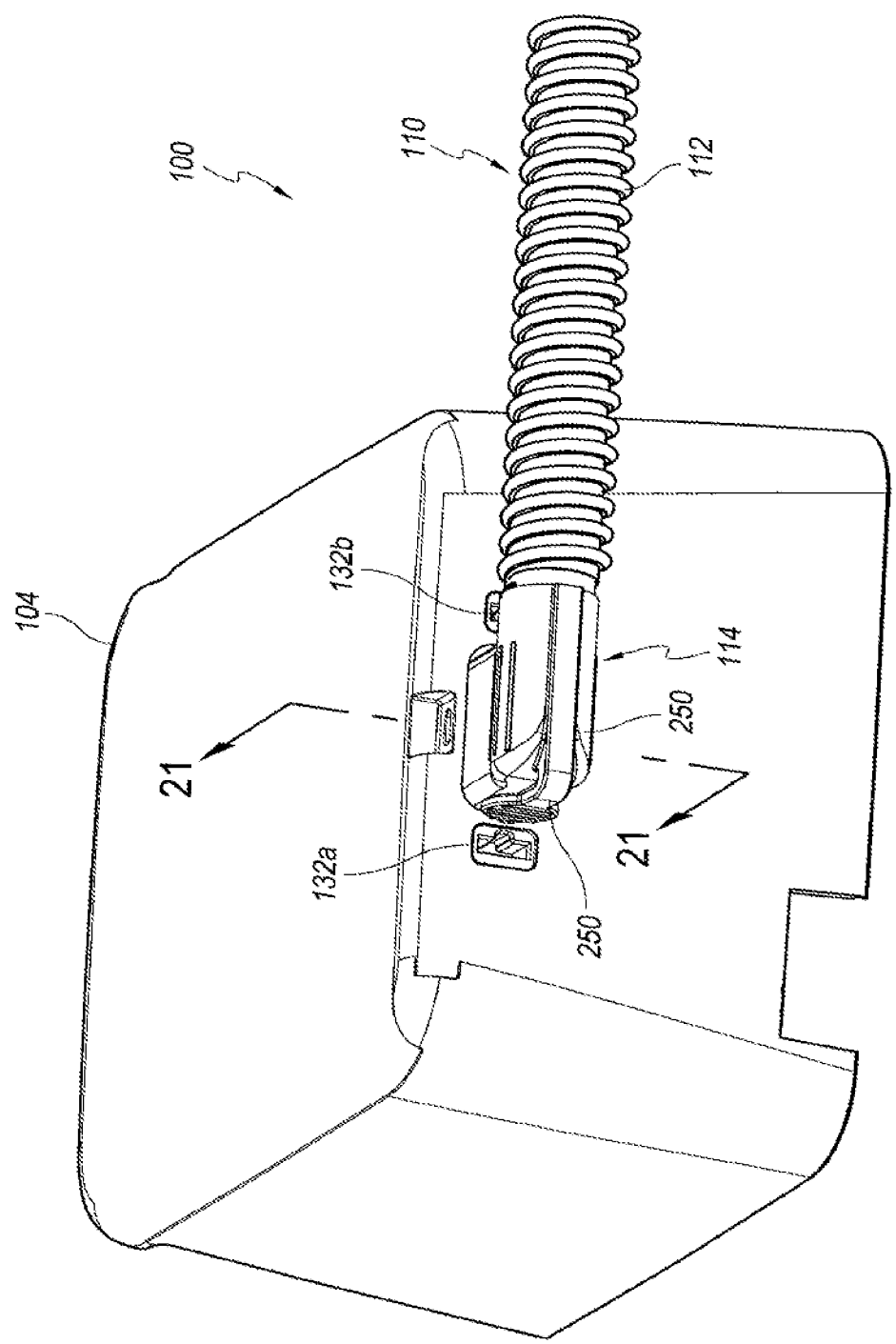
FIG. 19 is a perspective view of a flow generator and an alternative breathing tube assembly, relative to the assembly of FIGS. 16-18.
Figure 21:
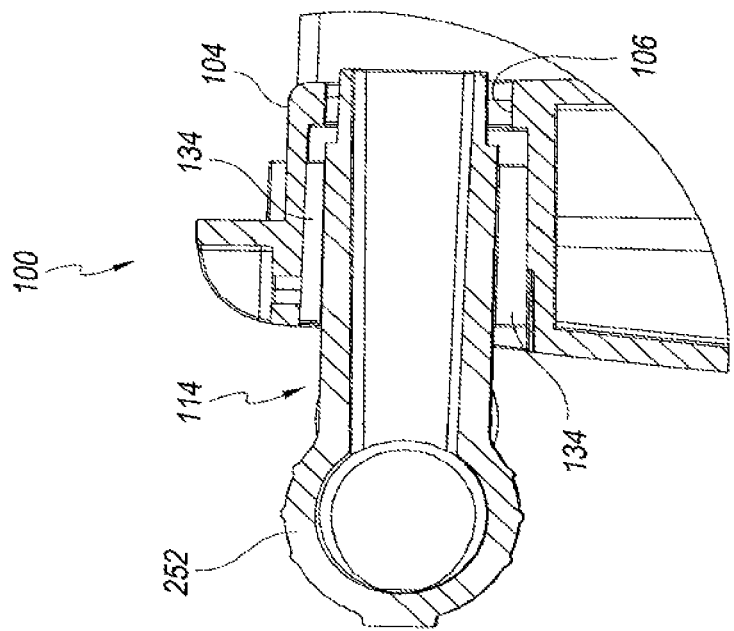
FIG. 21 is a sectional view of the flow generator and breathing tube assembly of FIG. 19 taken along line 21-21 of FIG. 19.
Figure 20:
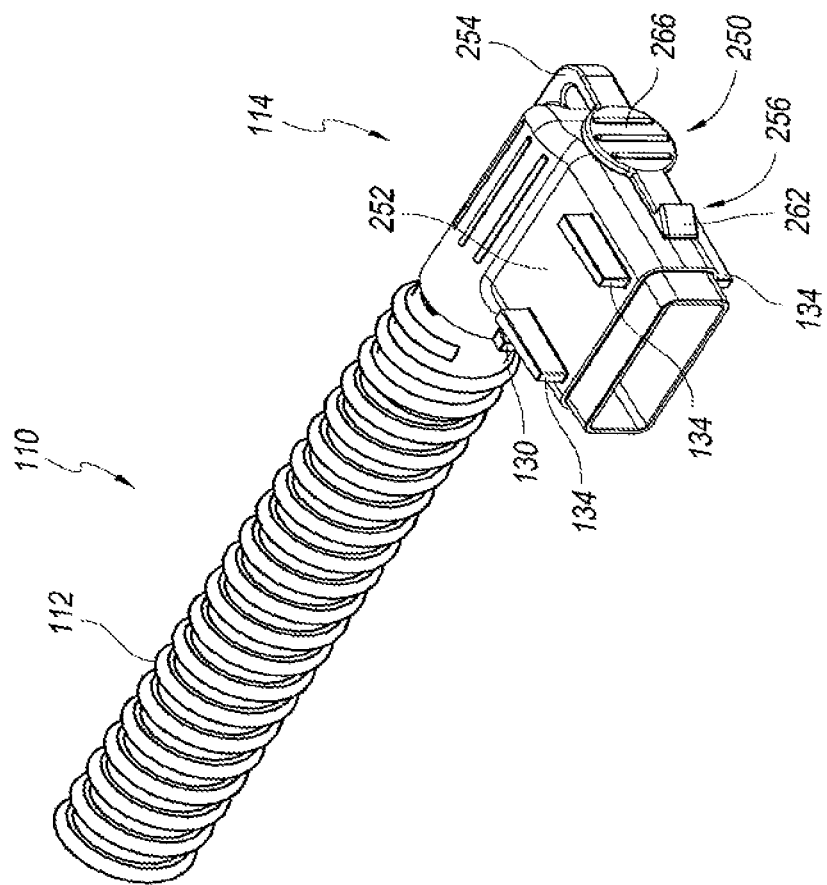
FIG. 20 is a perspective view of the breathing tube assembly of FIG. 19 separated from the flow generator.

The connector 114 of FIGS. 19-21 includes a single resilient arm 250 that extends along one side of the main body 252 of the connector 114. Preferably, the arm 250 extends along the opposite side of the main body 252 relative to the tube 112. In the illustrated arrangement, the fixed end 254 of the arm 250 originates at or near the rearward end of the main body 252 and has a length that is at least about one-half of a length of the main body 252. Preferably, the arm 250 is relatively slender in width with the exception of the finger grip portion 266, which is wider than the remainder of the arm 250, can be circular or generally circular in shape and can be located at approximately a mid-point between the fixed end 254 and the tab 262 located at the free end 256.

Figure 22:
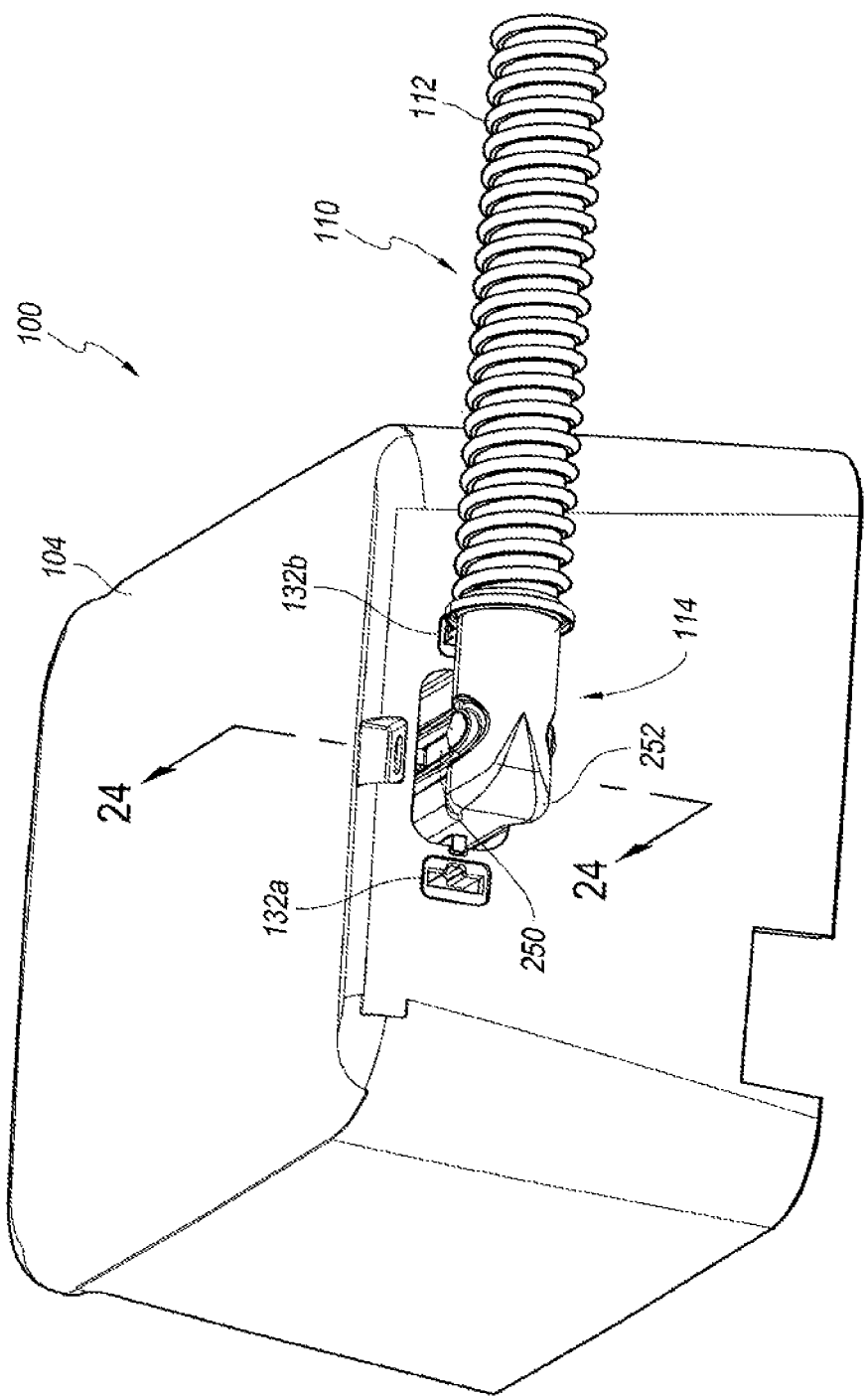
FIG. 22 is a perspective view of a flow generator and another alternative breathing tube assembly, relative to the assemblies of FIGS. 16-21.
Figure 24:
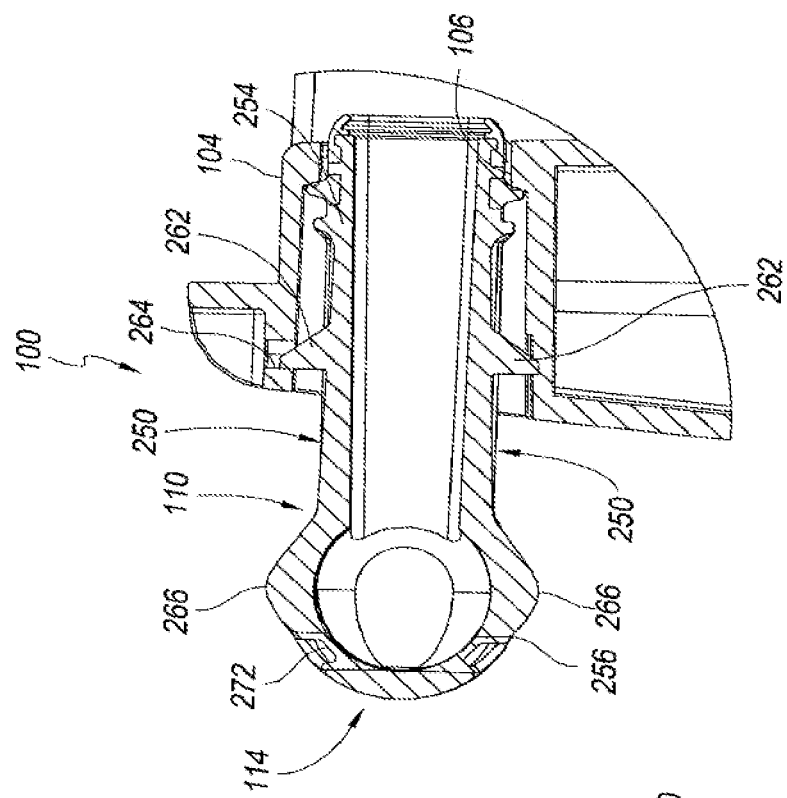
FIG. 24 is a sectional view of the flow generator and breathing tube assembly of FIG. 22 taken along line 24-24 of FIG. 22.
Figure 23:
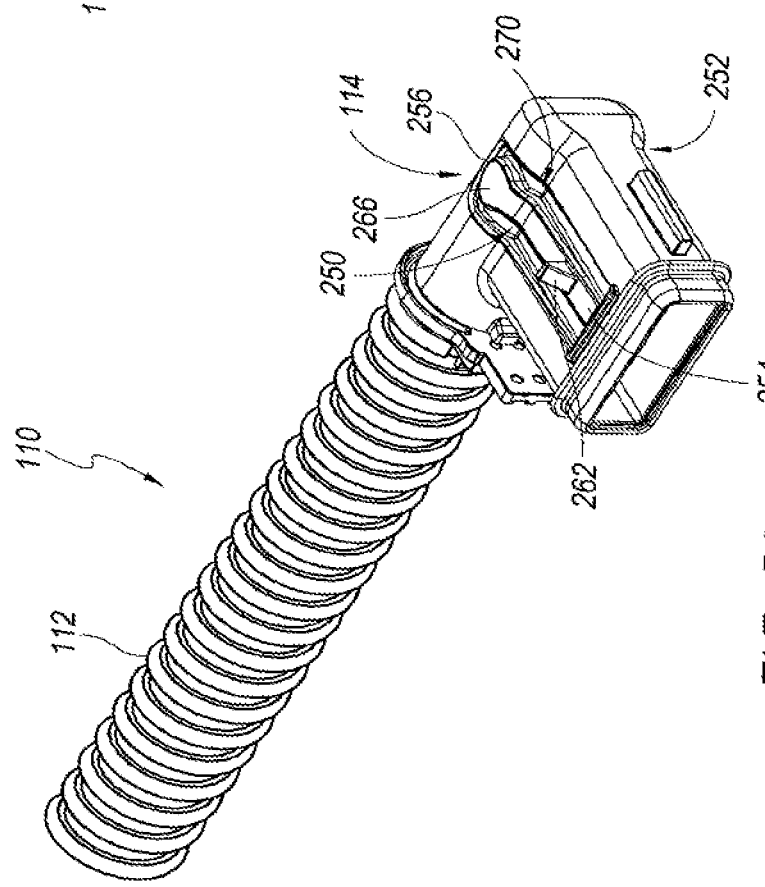
FIG. 23 is a perspective view of the breathing tube assembly of FIG. 22 separated from the flow generator.

The connector 114 of FIGS. 22-24 includes at least one, and preferably a pair, of resilient arms 250 on opposing sides of the main body 252. Preferably, the arms 250 are positioned within recessed central portions 270 such that the arms 250 are generally or substantially flush, or recessed within, surrounding portions of the main body 252. The fixed ends 254 are located closer the open end of the connector 114 relative to the free ends 256, which are located toward the rearward end of the main body 252. The tab 262 of each arm 250 is located between the fixed end 254 and the free end 256. Preferably, the finger grip portion 266 is located at or near the free end 256 of the arm 250. It is noted that the "free" ends 256 of the arms 250 in this connector 114 are not completely disconnected from the main body 252. Rather, the free ends 256 are connected to the main body 252 by a reduced-wall thickness portion 272 (FIG. 24) that permits movement of the free ends 256. In the illustrated arrangement, the reduced-wall thickness portion 272 also extends along the sides of the arms 250. Therefore, the term "free end" as used herein applies to movable ends of a flexible arm, which can be completely disconnected from a surrounding structure or can be arranged to permit enough movement of the "free end" relative to the surrounding structure to accomplish the designated task of the flexible arm (e.g., disconnection of the tab 262 from the recess or opening 264). In addition, the flexible arm need only be movable relative to surrounding structure such that the designated task can be accomplished.

Figure 25:
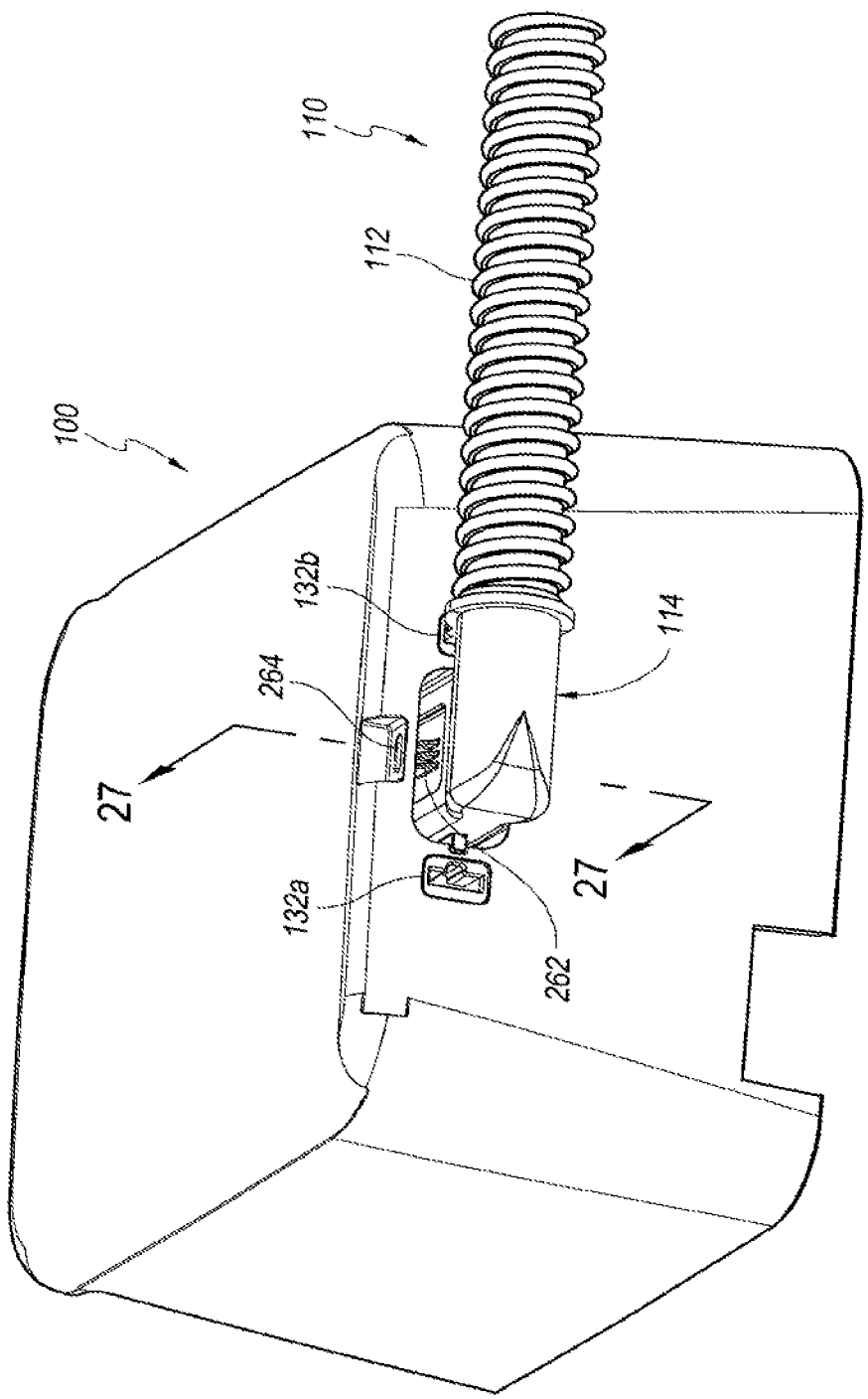
FIG. 25 is a perspective view of a flow generator and yet another alternative breathing tube assembly, relative to the assemblies of FIGS. 16-24.
Figure 27:
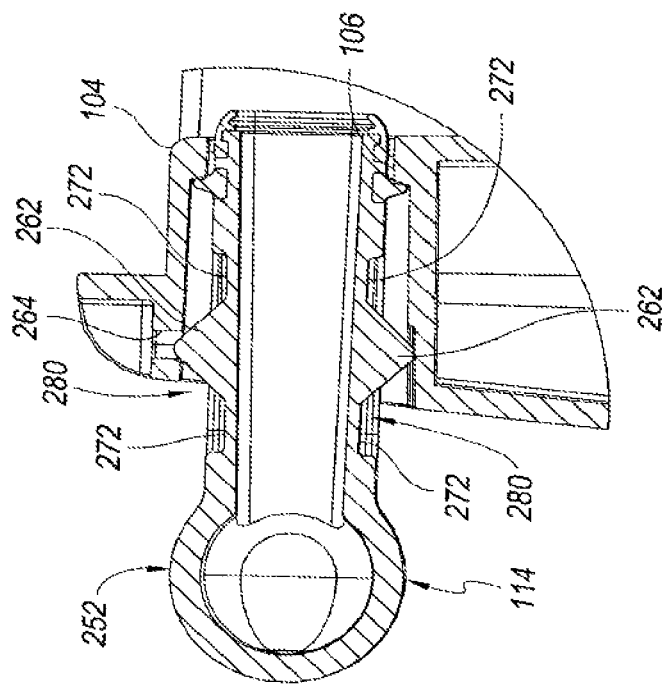
FIG. 27 is a sectional view of the flow generator and breathing tube assembly of FIG. 25 taken along line 27-27 of FIG. 25.
Figure 26:
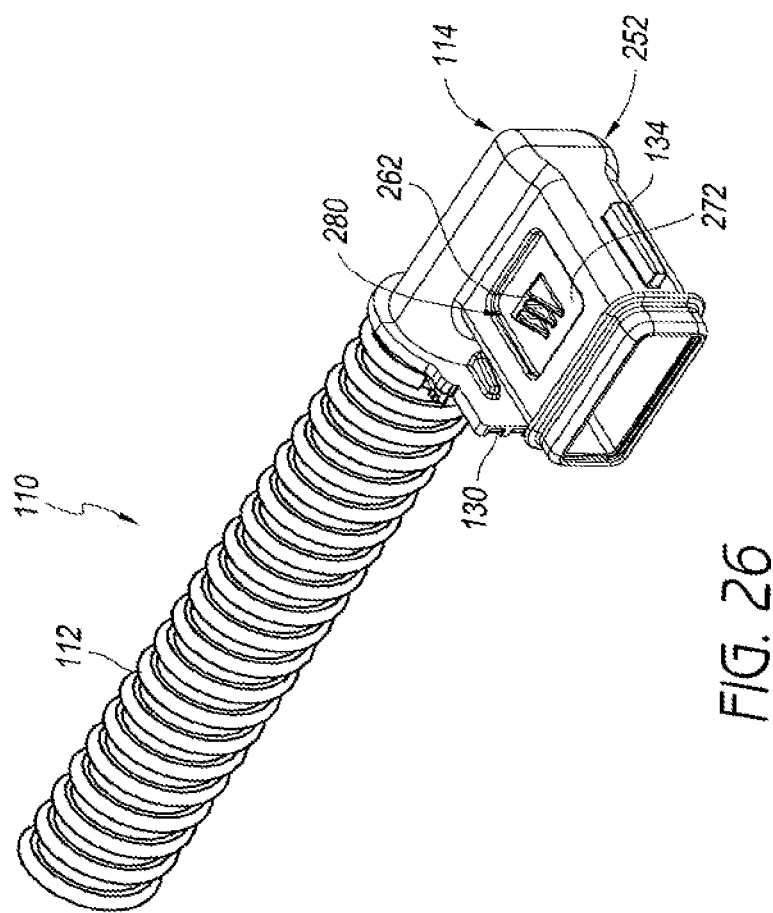
FIG. 26 is a perspective view of the breathing tube assembly of FIG. 25 separated from the flow generator.

The connector 114 of FIGS. 25-27 includes a resilient portion 280 that operates in a manner similar to the resilient arms 250 of the connector 114 of FIGS. 22-24. In the connector 114 of FIGS. 25-27, the resilient portion 280 carries the tab 262 and is movable relative to the main body 252 of the connector 114. In particular, the resilient portion 280 is partially or completely bounded by a reduced-wall thickness portion 272, which permits limited movement of the resilient portion 280, which preferably is enough movement to allow disengagement of the tab 262 from the recess or opening 264. The resilient portion 280 can be centrally-located within the main body 252 of the connector 114 such that the resilient portion 280 is completely surrounded by the main body 252. Preferably, two resilient portions 280 are provided on opposite sides (e.g., top and bottom) of the main body 252 of the connector 114.

FIGS. 28-30 illustrate another respiratory therapy system 100, including a flow generator 104 (e.g., CPAP device) and a breathing tube assembly 110. The system 100 of FIGS. 28-30 is similar to the systems 100 of FIGS. 1-15 and, therefore, the same reference numbers are used to indicate corresponding or similar components and only significant differences relative to the previously-described systems 100 are described in detail. Any components, assemblies or features not described in detail can be assumed to be identical or similar to the corresponding component, assembly or feature of any of the previous systems 100, or can be of any other suitable arrangement. Moreover, the system 100 can include any of the optional features (e.g., tab 200) of the systems 100 of FIGS. 1-15 that are not shown or described in the illustrated embodiment of FIGS. 28-30.

As in the prior systems 100 of FIGS. 1-15, the illustrated swivel elbow 116 urges, guides, constrains or otherwise directs a portion of the tube 112 into a bend, provides crush protection and permits the position of the tube 112 to be varied relative to the CPAP device 104. Preferably, the curved portion of the tube 112 is near or adjacent the connector 114. The connector engagement portion 142 of the illustrated swivel elbow 116 engages the connector 114 and the tube engagement portion 144 of the swivel elbow 116 engages the tube 112. In the illustrated arrangement, the connector engagement portion 142 and the tube engagement portion 144 are in the form of bands that substantially or entirely surround a circumference of the connector 114 and/or tube 112.

The tube guide portion 146 extends between the connector engagement portion 142 and the tube engagement portion 144. Preferably, the tube guide portion 146 defines a curved surface 150, which guides the tube 112 into a curved orientation. As described previously, the angular offset between the axis of the connector engagement portion 142 and the axis of the tube engagement portion 144 can be approximately 90 degrees or any of the angles previously described with respect to the elbows 116 of FIGS. 1-15.

In the illustrated arrangement, similar to the elbows 116 illustrated in FIGS. 1-15, the tube guide portion 146 only partially surrounds the tube 112. In particular, the illustrated tube guide portion 146 surrounds approximately or exactly half of the circumference of the tube 112. Preferably, unlike the elbows 116 of FIGS. 1-15, the tube guide portion 146 of FIGS. 28-30 is positioned at least partially on the inside of the tube 112 relative to the bend (e.g., the center point of the bend radius) such that the tube guide portion 146 is positioned to support at least a portion of the inside bend surface of the tube 112. Such an arrangement provides advantageous support and crush protection to the tube 112 and permits rotational adjustment of the tube 112 relative to the CPAP device 104, while facilitating easier manufacture of the elbow 116. Preferably, the tube guide portion 146 extends in a circumferential direction (relative to the tube 112) over the entire inside half of the tube 112. The illustrated tube guide portion 146 has a solid wall between its opposing (upper and lower) edges; however, the guide portion 146 could include one or more openings or windows therein (or be constructed from one or more axial portions) to reduce material or adjust the flexibility of the tube. As described above, although the tube guide portion 146 is illustrated as external to the tube 112, it could be internal in other arrangements.

As described above, preferably, the swivel elbow 116 is rotatable about at least the longitudinal axis of the outlet 106 of the CPAP device 104 to permit a position of the tube 112 to be varied relative to the CPAP device 104. In the illustrated arrangement, the swivel elbow 116 can be rotated 360 degrees about the axis of the outlet 106, and beyond. That is, the swivel elbow 116 can be rotated in a single direction for multiple rotations. However, in other arrangements, the rotation of the swivel elbow 116 may be limited, as described above.

The swivel elbow 116 of FIGS. 28-30 preferably also includes a feature or features that facilitate assembly and/or disassembly of the breathing tube assembly 110 to or from the CPAP device 104. For example, the illustrated swivel elbow 116 includes a tab 290 of a suitable size and shape to permit a user to grasp the tab 290 to facilitate assembly of the breathing tube assembly 110 to the CPAP device 104 or to facilitate removal of the breathing tube assembly 110 from the CPAP device 104. Preferably, the tab 290 is located on or near the connector engagement portion 142 of the swivel elbow 116 or is otherwise oriented generally perpendicular to a longitudinal axis of a connection portion of the breathing tube assembly 110 that is adjacent the outlet 106 of the CPAP device 104. Preferably, the tab 290 is oriented generally perpendicularly relative to the axis of the outlet 106 and/or an outer surface of the CPAP device 104 surrounding or adjacent to the outlet 106.

In the illustrated arrangement, the tab 290 is positioned on the outside of the swivel elbow 116 (the outside of the bend) and/or on the side of the elbow 116 opposite the tube engagement portion 144. Advantageously, with such an arrangement, a user can grasp both the tab 290 and the tube engagement portion 144 of the swivel elbow 166 to apply an even or balanced force to the tube assembly 110 that is substantially aligned with the axis of the connector 114 and/or the outlet 106 to facilitate assembly or disassembly of the breathing tube assembly 110 to or from the CPAP device 104. Manufacture and assembly of the breathing tube 110, assembly of the tube 110 to the CPAP (or other) device 104 and operation of the system 100 preferably is substantially similar or identical to that described above with reference to FIGS. 1-15.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

What is claimed is:

1. A breathing tube assembly comprising:
   a breathing tube, and
   a connector coupled to the breathing tube arranged to non-rotatably connect the breathing tube to an outlet of a flow generator,
   a swivel elbow rotatably coupled to the connector, the swivel elbow comprising:
      a connector engagement portion including a connector band that engages a circumference of the connector,
      a tube engagement portion including a tube band that engages a circumference of the breathing tube, and
      a tube guide portion that extends between the connector engagement portion and the tube engagement portion;
   wherein the breathing tube comprises a first end that is coupled to the connector in a non-rotatable manner; and
   wherein the swivel elbow is rotatable relative to the connector and is also rotatable relative to the breathing tube such that the swivel elbow can be rotated relative to the flow generator to vary a direction in which the breathing tube extends relative to the flow generator.

2. The breathing tube assembly of claim 1, wherein the breathing tube has a second end that is configured to be attached to a patient interface.

3. The breathing tube assembly of claim 1, wherein the connector band surrounds an entire circumference of the connector.

4. The breathing tube assembly of claim 1, wherein the connector band includes a connector band slit, such that the connector band does not entirely surround the circumference of the connector.

5. The breathing tube assembly of claim 1, wherein the tube band surrounds an entire circumference of the breathing tube.

6. The breathing tube assembly of claim 1, wherein the tube band includes a tube band slit, such that the tube band does not entirely surround the circumference of the tube.

7. The breathing tube assembly of claim 1, wherein the tube guide portion defines a curved surface arranged to guide the tube into a curved orientation such that the tube has an inside curved surface and an outside curved surface.

8. The breathing tube assembly of claim 1, wherein an axis of the connector engagement portion is offset at an angle relative to an axis of the tube engagement portion.

9. The breathing tube assembly of claim 8, wherein the angle is 90 degrees.

10. The breathing tube assembly of claim 8, wherein the angle is within a range of between 45 degrees to 180 degrees.

11. The breathing tube assembly of claim 8, wherein the angle is adjustable.

12. The breathing tube assembly of claim 1, wherein at least the tube guide portion of the swivel elbow has greater resistance to bending relative to the tube.

13. The breathing tube assembly of claim 1, wherein the tube guide portion at least partially surrounds a circumference of the breathing tube.

14. The breathing tube assembly of claim 1, wherein the tube guide portion surrounds half of the circumference of the breathing tube.

15. The breathing tube assembly of claim 1, wherein the tube guide portion is configured to shield the tube by contacting a wall or other object instead of the breathing tube contacting the wall or other object, thereby reducing the likelihood of partial or complete occlusion of the tube.

16. The breathing tube assembly of claim 1, wherein the tube guide portion is positioned at least partially adjacent an inside curved surface of the breathing tube such that the tube guide portion is positioned to support at least a portion of the inside curved surface of the breathing tube.

17. The breathing tube assembly of claim 1, wherein the tube guide portion includes one or more openings or windows therein.

18. The breathing tube assembly of claim 1, wherein the connector includes:
   a flange, and
   a shaft extending from the flange, the shaft defining a connector internal passage that communicates with an interior passage of the breathing tube.

19. The breathing tube assembly of claim 18, wherein the connector includes an electrical terminal extending from the flange, and wherein the electrical terminal is connected to an electrical circuit that is integrated into the breathing tube.

20. The breathing tube assembly of claim 1, wherein the swivel elbow includes a tab positioned on an outside of a curve of the swivel elbow.

21. The breathing tube assembly of claim 1, wherein the connector is permanently coupled to the breathing tube.

22. A respiratory therapy system for providing respiratory therapy to a user comprising:
   a flow generator that generates a flow of a breathing gas, the breathing tube assembly of claim 1, wherein the breathing tube assembly is arranged to deliver the flow of breathable gas to a patient interface.

\* \* \* \* \*